(12) United States Patent
Luithle et al.

(10) Patent No.: US 7,138,410 B2
(45) Date of Patent: Nov. 21, 2006

(54) AZA-BICYCLIC N-BIARYLAMIDES WITH AFFINITY FOR THE α7 NICOTINIC ACETYLCHOLINE RECEPTOR

(75) Inventors: Joachim Luithle, Wülfrath (DE); Frank-Gerhard Böss, Berkshire (GB); Christina Erb, Kriftel (DE); Katrin Schnizler, Rodenbach (DE); Timo Flessner, Wuppertal (DE); Marja van Kampen, Düsseldorf (DE); Christoph Methfessel, Wuppertal (DE); Frank-Thorsten Hafner, Wuppertal (DE)

(73) Assignee: Bayer HealthCare AG, Leverkusen (DE)

( * ) Notice: Subject to any disclaimer, the term of this patent is extended or adjusted under 35 U.S.C. 154(b) by 57 days.

(21) Appl. No.: 10/508,108

(22) PCT Filed: Mar. 3, 2003

(86) PCT No.: PCT/EP03/02153

§ 371 (c)(1),
(2), (4) Date: Mar. 3, 2005

(87) PCT Pub. No.: WO03/078431

PCT Pub. Date: Sep. 25, 2003

(65) Prior Publication Data

US 2005/0154045 A1    Jul. 14, 2005

(30) Foreign Application Priority Data

Mar. 15, 2002 (DE) ............ 102 11 415

(51) Int. Cl.
A61K 31/439 (2006.01)
A61K 31/5377 (2006.01)
C07D 453/02 (2006.01)
C07D 413/12 (2006.01)

(52) U.S. Cl. ............... 514/305; 514/235.2; 546/133; 544/127

(58) Field of Classification Search ............ 546/133; 544/127

See application file for complete search history.

(56) References Cited

U.S. PATENT DOCUMENTS 5,998,429 A     12/1999  Macor et al.
2002/0123507 A1 *  9/2002  Lauffer et al. ............ 514/305

* cited by examiner

Primary Examiner—Kamal A. Saeed
Assistant Examiner—Jason M. Nolan
(74) Attorney, Agent, or Firm—Susan M. Pellegrino

(57) ABSTRACT

The invention relates to novel 1-aza-bicyclic N-biarylamides, methods for production and use thereof for the production of medicaments for the treatment and/or prophylaxis of diseases and for improving perception, concentration, learning ability and memory.

13 Claims, No Drawings

AZA-BICYCLIC N-BIARYLAMIDES WITH AFFINITY FOR THE α7 NICOTINIC ACETYLCHOLINE RECEPTOR

The invention relates to novel bicyclic N-biarylamides, to a process for the preparation thereof and to the use thereof for producing medicaments for the treatment and/or prophylaxis of diseases and for improving perception, concentration, learning and/or memory.

Nicotinic acetylcholine receptors (nAChR) form a large family of ion channels which are activated by the messenger acetylcholine which is produced in the body (Galzi and Changeux, *Neuropharmacol.* 1995, 34, 563–582). A functional nAChR consists of five subunits which may be different (certain combinations of α1-9 and β1-4,γ,δ,ε subunits) or identical (α7-9). This leads to the formation of a diversity of subtypes which differ in the distribution in the muscles, the nervous system and other organs (McGehee and Role, *Annu. Rev. Physiol.* 1995, 57, 521–546). Activation of nAChR leads to influx of cations into the cell and to stimulation of nerve cells or muscle cells. Selective activation of individual ntAChR subtypes restricts this stimulation to the cell types which have a corresponding subtype and is thus able to avoid unwanted side effects such as, for example, stimulation of nAChR in the muscles. Clinical experiments with nicotine and experiments in various animal models indicate that central nicotinic acetylcholine receptors are involved in learning and memory processes (e.g. Rezvani and Levin, *Biol. Psychiatry* 2001, 49, 258–267). Nicotinic acetylcholine receptors of the alpha7 subtype (α7 nAChR) have a particularly high concentration in regions of the brain which are important for learning and memory, such as the hippocampus and the cerebral cortex (Séguéla et al., *J. Neurosci.* 1993, 13, 596–604). The α7 nAChR has a particularly high permeability for calcium ions, increases glutamatergic neurotransmission, influences the growth of axons and, in this way, modulates neuronal plasticity (Broide and Leslie, *Mol. Neurobiol.* 1999, 20, 1–16).

Certain quinuclidinecarboxanilides are described as antiarrhythmics and local anesthetics (cf., for example, FR 1.566.045, GB 1 578 421 and Oppenheimer et al., *Life Sci.* 1991, 48, 977–985).

WO 01/60821 discloses biarylcarboxamides with affinity for the α7 nAChR for the treatment of learning and perception impairments.

The present invention relates to compounds of the general formula (I)

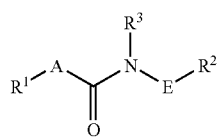

in which
R$^1$ is a 1-azabicyclo[m.n.p]alkyl radical having 7 to 11 ring atoms,
  in which m and n are independently of one another 2 or 3,
  in which p is 1, 2 or 3,
  and where the bicycloalkyl radical is optionally substituted by (C$_1$–C$_6$)-alkyl,
A is a bond, methylene, ethylene or propylene,
E is divalent, 5- to 6-membered heteroaryl or benzenediyl, where heteroaryl and benzenediyl are optionally substituted by radicals selected from the group of halogen, cyano, trifluoromethyl, trifluoromethoxy and (C$_1$–C$_6$)-alkyl,
R$^2$ is 5- to 6-membered heteroaryl or phenyl, where heteroaryl and phenyl are optionally substituted by radicals selected from the group of halogen, 5- to 6-membered heterocyclyl, —CO—NR$^4$R$^5$, —CO—OR$^6$, —NR$^7$R$^8$, —NR$^9$—CO—R$^{10}$, —COR$^{13}$, cyano, trifluoromethyl, trifluoromethoxy, nitro, optionally hydroxyl-, amino-, —NH—CO—R$^{11}$—, —O—CO—NHR$^{14}$—, halogen- or cyano-substituted (C$_1$–C$_6$)-alkyl, (C$_1$–C$_6$)-alkoxy and (C$_1$–C$_6$)-alkylthio,
  in which R$^4$, R$^5$, R$^6$, R$^7$, R$^8$, R$^9$, R$^{10}$, R$^{11}$, R$^{13}$ and R$^{14}$ are independently of one another hydrogen, (C$_1$–C$_6$)-alkyl, phenyl or benzyl, and
R$^3$ is hydrogen or (C$_1$–C$_6$)-alkyl, and the salts, solvates and solvates of the salts thereof.

The compounds of the invention may depending on their structure exist in stereoisomeric forms (enantiomers, diastereomers). The invention relates therefore to the enantiomers or diastereomers and there respective mixtures. These mixtures of enantiomers and/or diastereomers can be separated in a known manner to isolate the stereoisomerically pure constituents.

The compounds of the invention may also be in the form of their salts, solvates or solvates of the salts.

Salts which are preferred for the purposes of the invention are physiologically acceptable salts of the compounds of the invention.

Physiologically acceptable salts of the compounds of the invention may be acid addition salts of the compounds with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

However, salts which may be mentioned are also salts with conventional bases, such as, for example, alkali metal salts (e.g. sodium or potassium salts), alkaline earth metal salts (e.g. calcium or magnesium salts) or ammonium salts derived from ammonia or organic amines such as, for example, diethyl amine, triethylamine, ethyldiisopropylamine, procaine, dibenzylamine, N-methylmorpholine, dihydroabietylamine 1-ephenamine or N-methylpiperidine.

Solvates is the term used for the purposes of the invention for those forms of the compounds which form a complex with solvent molecules by coordination in the solid or liquid state. Hydrates are a special form of solvates in which the coordination takes place with water.

For the purposes of the present invention, the substituents generally have the following meaning:

(C$_1$–C$_6$)- and (C$_1$–C$_4$-alkoxy stands for a straight-chain or branched alkoxy radical respectively having 1 to 6 and 1 to 4 carbon atoms. Preference is given to a straight-chain or branched alkoxy radical having 1 to 4, particularly preferably having 1 to 3, carbon atoms. The following may be mentioned by way of example and preferably: methoxy, ethoxy, n-propoxy, isopropoxy, tert-butoxy, n-pentoxy and n-hexoxy.

(C$_1$–C$_6$)- and (C$_1$–C$_4$)-alkyl stand for a straight-chain or branched or branched alkyl radical respectively having 1 to 6 and 1 to 4 carbon atoms. Preference is given to a straight-chain or branched alkyl radical having 1 to 4, particularly preferably having 1 to 3, carbon atoms. The following may be mentioned by way of example and preferably: methyl, ethyl, n-propyl, isopropyl, tert-butyl, n-pentyl and n-hexyl.

$(C_1-C_6)$-alkylthio stands for a straight-chain or branched alkylthio radical having 1 to 6 carbon atoms. Preference is given to a straight-chain or branched alkylthio radical having 1 to 4, particularly preferably having 1 to 3, carbon atoms. The following may be mentioned by way of example and preferably: methylthio, ethylthio, n-propylthio, isopropylthio, tert-butylthio, n-pentylthio and n-hexylthio.

The 1-azabicyclo[m.n.p]alkyl radical having 7 to 11 ring atoms is preferably and by way of example: 1-azabicyclo[3.2.1]octyl(isotropane), 1-azabicyclo[3.3.1]nonyl (isogranatane), 1-azabicyclo[2.2.2]octyl (quinuclidine).

Halogen stands for fluorine, chlorine, bromine and iodine. Fluorine, chlorine and bromine are preferred. Fluorine and chlorine are particularly preferred.

5- to 6-membered heteroaryl stands for an aromatic radical having 5 to 6 ring atoms and up to 4, preferably up to 2, heteroatoms from the series S, O and/or N. The heteroaryl radical may be bonded via a carbon atom or heteroatom. The following may be mentioned by way of example and preferably: thienyl, furyl, pyrrolyl, thiazolyl, oxazolyl, imidazolyl, pyridyl, pyrimidinyl, and pyridazinyl.

Divalent 5- to 6-membered heteroaryl stands for a divalent aromatic radical having 5 to 6 ring atoms and up to 4, preferably up to 2, heteroatoms from the series of S, O and/or N. The heteroaryl radical may be bonded via a carbon atom or heteroatom. The following may be mentioned by way of example and preferably: thiophenediyl, furandiyl, pyrrolediyl, thiazolediyl, oxazolediyl, imidazolediyl, pyridinediyl, pynmidinediyl, and pyridazinediyl.

5- to 6-membered heterocyclyl stands for a heterocyclic radical having 5 to 6 ring atoms and up to 3, preferably 2, heteroatoms or hetero groups from the series of N, O, S, SO, $SO_2$, with preference for N and O. The heterocyclyl radicals may be saturated or partially unsaturated. Saturated heterocyclyl radicals are preferred. The heterocyclyl radicals may be bonded via a carbon atom or a heteroatom. Nonlimiting examples include pyrrolinyl, tetrahydrofuranyl, tetrahydrothienyl, pyranyl, piperidinyl, piperazinyl, thiopyranyl, morpholinyl.

If radicals in the compounds of the invention are optionally substituted, the radicals may, unless specified otherwise, be substituted one or more times, identically or differently. Substitution with up to three identical or different substituents is preferred.

Preference is given to compounds of the formula (I), in which
$R^1$ is 1-azabicyclo[2.2.2]oct-3-yl,
A is a bond or methylene,
E is benzenediyl which is optionally substituted by a radical selected from the group of fluorine, chlorine, cyano, methyl and trifluoromethyl,
$R^2$ is thienyl or phenyl, where the rings are optionally substituted by up to 2 radicals selected from the group of halogen, cyano, trifluoromethyl, trifluoromethoxy, nitro, morpholinyl, $(C_1-C_4)$-alkyl, $(C_1-C_4)$-alkoxy, $(C_1-C_4)$-alkylthio, —CO—$NR^4R^5$, —CO—$OR^6$, —$NR^9$—CO—$R^{10}$ and —CO—$R^{13}$,
where $(C_1-C_4)$-alkyl is optionally substituted by hydroxy, halogen and —O—CO—$NHR^{14}$,
where $R^4$, $R^5$, $R^6$, $R^9$, $R^{10}$, $R^{13}$ and $R^{14}$ are independently of one another hydrogen or $(C_1-C_4)$-alkyl, and
$R^3$ is hydrogen, and the salts, solvates and solvates of the salts thereof.

Particularly preferred compounds of the general formula (I) are those in which
$R^1$ is 1-azabicyclo[2.2.2]octyl.
Particularly preferred compounds of the general formula (I) are those in which
$R^1$ is 1-azabicyclo[2.2.2]oct-3-yl.
Likewise preferred compounds of the general formula (I) are those in which
A is a bond or methylene.
Particularly preferred compounds of the general formula (I) are those in which
A is a bond.
Likewise preferred compounds of the general formula (I) are those in which
E is benzenediyl which is optionally substituted by 1 to 3 radicals selected from the group of fluorine, chlorine, cyano, methyl and trifluoromethyl.
Particularly preferred compounds of the general formula (I) are those in which
E is benzenediyl.
Likewise preferred compounds of the general formula (I) are those in which
$R^2$ is thienyl or phenyl, where the rings are optionally substituted by 1 to 3 radicals selected from the group of halogen, cyano, trifluoromethyl, trifluoromethoxy, nitro, $(C_1-C_4)$-alkyl, hydroxymethyl, and $(C_1-C_4)$-alkoxy.
Particularly preferred compounds of the general formula (I) are those in which
$R^2$ is hydroxymethylphenyl.
Likewise preferred compounds of the general formula (I) are those in which
$R^3$ is hydrogen or methyl.
Particularly preferred compounds of the general formula (I) are those in which
$R^3$ is hydrogen.
Combinations of two or more of the abovementioned preferred ranges are very particularly preferred.
Likewise very particularly preferred are compounds of the general formula (I) in which
$R^1$ is 1-azabicyclo[2.2.2]oct-3-yl,
A is a bond,
E is benzenediyl which is optionally substituted by 1 to 3 radicals selected from the group of fluorine, chlorine, cyano, methyl and trifluoromethyl,
$R^2$ is thienyl or phenyl, where the rings are optionally substituted by 1 to 3 radicals selected from the group of halogen, cyano, trifluoromethyl, trifluoromethoxy, nitro, $(C_1-C_4)$-alkyl, hydroxymethyl, and $(C_1-C_4)$-alkoxy, and
$R^3$ is hydrogen.

The invention further relates to a process for preparing the compounds of the formula (I), characterized in that
[A] compounds of the general formula (II)

in which
$R^1$ and A have the meanings indicated above, and
X is hydroxy or a suitable leaving group such as, for example, chlorine or pentafluorophenoxy,
are reacted with a compound of the general formula (III)

$R^3$—NH-E-$R^2$         (III), in which

R², R³ and E have the meanings indicated above, in an inert solvent, where appropriate in the presence of a condensing agent, and where appropriate in the presence of a base, or

[B] compounds of the general formula (II) are initially reacted with a compound of the general formula (IV)

in which

R³ and E have the meanings indicated above, and

Y is a suitable leaving group such as, for example, triflate or halogen, preferably bromine or iodine, where appropriate in an inert solvent, where appropriate in the presence of a condensing agent, and where appropriate in the presence of a base, to give compounds of the general formula (V)

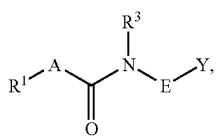

in which

R¹, R³, A, E and Y have the meanings indicated above, and the latter are then reacted in a coupling reaction with compounds of the general formula (VI)

in which

R² has the meanings indicated above, and

R¹² is hydrogen or methyl, or the two radicals together form a $CH_2CH_2$ or $C(CH_3)_2-C(CH_3)_2$ bridge, in an inert solvent in the presence of a suitable catalyst and in the presence of a base, and the resulting compounds of the formula (I) are reacted where appropriate with the appropriate (i) solvents and/or (ii) bases or acids to give the solvates, salts and/or solvates of the salts thereof.

If X is a leaving group, chloro, mesyloxy and isobutyloxycarbonyloxy, in particular chloro, are preferred.

Examples of inert solvents for process steps (II)+(III)→(I) and (II)+(IV)→(V) are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, ethyl acetate, acetone, dimethylformamide, dimethylacetamide, dimethyl sulfoxide, acetonitrile or pyridine, with preference for dimethylformamide, tetrahydrofuran, methylene chloride or chloroform.

Condensing agents for process steps (II)+(III)→(I) and (II)+(IV)→(V) are, for example, carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS-carbodiimide) or carbonyl compounds such as carbonyldiimidazole, or 1,2-oxazolium compounds such as 2-ethyl-5-phenyl-1,2-oxazolium-3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU) or benzotriazol-1-yloxytris(dimethylamino)phosphonium hexafluorophosphate (BOP), or mixtures thereof.

It may be advantageous where appropriate to use these condensing agents in the presence of an auxiliary nucleophile such as, for example, 1-hydroxybenzotriazole (HOBt).

Particular preference is given to HATU or the combination of N-(3-dimethylaminoisopropyl) -N'-ethylcarbodiimide hydrochloride (EDC) and 1-hydroxybenzotriazole (HOBt) in dimethylformamide.

Examples of bases for process steps (II)+(III)→(I) and (II)+(IV)→(V) are alkali metal carbonates such as, for example, sodium or potassium carbonate or bicarbonate, or organic bases such as trialkylamines, e.g. triethylamine, N-methylmorpholine, N-methylpiperidine, 4-dimethylaminopyridine or diisopropylethylamine.

Process steps (II)+(III)→(I) and (II)+(IV)→(V) are preferably carried out in a temperature range from room temperature to 50° C. under atmospheric pressure.

Examples of inert solvents for process step (V)+(VI)→(I) are ethers such as dioxane, tetrahydrofuran or 1,2-dimethoxyethane, hydrocarbons such as benzene, xylene or toluene, or other solvents such as nitrobenzene, dimethylformamide, dimethylacetamide, dimethyl sulfoxide or N-methylpyrrolidone. Solvents such as, for example, dimethylformamide, dimethylacetamide, dimethyl sulfoxide or 1,2-dimethoxyethane are preferred.

Examples of catalysts suitable for process step (V)+(VI)→(I) are the palladium catalysts usual for Suzuki couplings, with preference for catalysts such as, for example, dichlorobis(triphenylphosphine)palladium, tetrakistriphenylphosphinepalladium, palladium(II) acetate or bis(diphenylphosphino)ferrocenepalladium(II) chloride (cf., for example, A. Suzuki, *Acc. Chem. Res.* 1982, 15, 178ff; Miyaura et al., *J. Am. Chem. Soc.* 1989, 111, 314).

Examples of bases suitable for process step (V)+(VI)→(I) are potassium acetate, cesium, potassium or sodium carbonate, barium hydroxide, potassium tert-butoxide, cesium fluoride or potassium phosphate. Cesium carbonate or sodium carbonate is preferred.

Process step (V)+(VI)→(I) is preferably carried out in a temperature range from room temperature to 130° C. under atmospheric pressure.

The compounds of the general formulae (II) and (VI) are known or can be synthesized by known processes from appropriate precursors [cf., for example, for compounds of the general formula (II): Kato et al., *Chem. Pharm. Bull.* 1995, 43, 1351–1357; Orlek et al., *J. Med. Chem.* 1991, 34, 2726–2735; Plate et al., *Bioorg. Med. Chem.* 2000, 8, 449–454; for compounds of the general formula (VI): D. S. Matteson, in: *Stereodirected Synthesis with Organoboranes*, editors K. Hafner, C. W. Rees, B. M. Trost, J.-M. Lehn, P. v. Ragué Schleyer, Springer-Verlag, Heidelberg 1995; H. C.

Brown, G. W. Kramer, A. B. Levy, M. M. Midland, *Organic Synthesis via Boranes*, Wiley, New York 1975; A. Pelter, K. Smith, H. C. Brown, *Borane Reagents*, Academic Press, London 1988].

The compounds of the general formulae (III) and (IV) are likewise known or can be synthesized by known processes from appropriate precursors (cf., for example, *Comprehensive Heterocyclic Chemistry*, Katritzky et al., editors, Elsevier, 1996). Thus, for example, benzoic acid derivatives can be converted as shown in the following synthesis scheme via rearrangement (Curtius degradation) of the corresponding carbonyl azides into the corresponding aniline derivatives (cf., for example, S. Deprets, G. Kirsch, *Eur. J. Org. Chem.* 2000, 7, 1353ff.):

Synthesis scheme

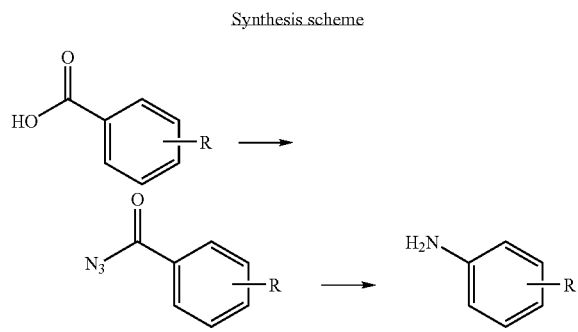

The compounds of the invention of the general formula (I) are suitable for use as medicaments for the treatment and/or prophylaxis of diseases in humans and/or animals.

The compounds of the invention show a valuable range of pharmacological effects which could not have been predicted.

They are notable as ligands, especially agonists, on the α7 nAChR.

The compounds of the invention can, because of their pharmacological properties, be employed alone or in combination with other medicaments for the treatment and/or prevention of cognitive impairments, especially of Alzheimer's disease. Because of their selective effect as α7 nAChR agonists, the compounds of the invention are particularly suitable for improving perception, concentration, learning or memory, especially after cognitive impairments like those occurring for example in situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic craniocerebral trauma, general concentration impairments, concentration impairments in children with learning and memory problems, attention deficit hyperactivity disorder, Alzheimer's disease, Lewy body dementia, dementia with degeneration of the frontal lobes, including Pick's syndrome, Parkinson's disease, progressive nuclear palsy, dementia with corticobasal degeneration, amyotrophic lateral sclerosis (ALS), Huntington's disease, multiple sclerosis, thalamic degeneration, Creutzfeld-Jacob dementia, HIV dementia, schizophrenia, schizophrenia with dementia or Korsakoff's psychosis.

The compounds of the invention can be employed alone or in combination with other active ingredients for the prevention and treatment of the sequelae of neurodegenerative disorders. Nonlimiting examples which may be mentioned of neurodegenerative disorders are Alzheimer's disease and Parkinson's disease.

The compounds of the invention can be employed alone or in combination with other medicaments for the prophylaxis and treatment of acute and/or chronic pain (for a classification, see "Classification of Chronic Pain, Descriptions of Chronic Pain Syndromes and Definitions of Pain Terms", 2nd edition, Meskey and Begduk, editors; IASP Press, Seattle, 1994), especially for the treatment of cancer-induced pain and chronic neuropathic pain like, for example, that associated with diabetic neuropathy, postherpetic neuralgia, peripheral nerve damage, central pain (for example as a consequence of cerebral ischaemia) and trigeminal neuralgia, and other chronic pain such as, for example, lumbago, backache (low back pain) or rheumatic pain. In addition, these substances are also suitable for the therapy of primary acute pain of any origin and of secondary states of pain resulting therefrom, and for the therapy of states of pain which were formerly acute and have become chronic.

The in vitro effect of the compounds of the invention can be shown in the following assays:

1. Determination of the Affinity of Test Substances for α7 nAChR by Inhibition of [$^3$H]-methyllycaconitine Binding to Rat Brain Membranes The [$^3$H]-methyllycaconitine binding assay is a modification of the method described by Davies et al. (*Neuropharmacol.* 1999, 38, 679–690).

Rat brain tissue (hippocampus or whole brain) is homogenized in homogenization buffer (10% w/v, 0.32 M sucrose, 1 mM EDTA, 0.1 mM phenylmethylsulfonyl fluoride (PMSF), 0.01% (w/v) NaN$_3$, pH 7.4, 4° C.) at 600 rpm in a glass homogenizer. The homogenate is centrifuged (1000×g, 4° C., 10 min) and the supernatant is removed. The pellet is resuspended (20% w/v) and the suspension is centrifuged (1000×g, 4° C., 10 min). The two supernatants are combined and centrifuged (15 000×g, 4° C., 30 min). The pellet obtained in this way is referred to as the P2 fraction.

The P2 pellet is washed twice with binding buffer (50 mM Tris-HCl, 1 mM MgCl$_2$, 120 mM NaCl, 5 mM KCl, 2 mM CaCl$_2$, pH 7.4), and centrifuged (15 000×g, 4° C., 30 min).

The P2 membranes are resuspended in binding buffer and incubated in a volume of 250 μl (amount of membrane protein 0.1–0.5 mg) in the presence of 1–5 nM [$^3$H]-methyllycaconitine, 0.1% (w/v) BSA (bovine serum albumin) and various concentrations of the test substance at 21° C. for 2.5 h. The nonspecific binding is determined by incubation in the presence of 1 μM α-bungarotoxin or 100 μM nicotine or 10 μM MLA (methyllycaconitine).

The incubation is stopped by adding 4 ml of PBS (20 mM Na$_2$HPO$_4$, 5 mM KH$_2$PO$_4$, 150 mM NaCl, pH 7.4, 4° C.) and filtering through type A/E glass fibre filters (Gelman Sciences) which have previously been placed in 0.3% (v/v) polyethyleneimine (PEI) for 3 h. The filters are washed twice with 4 ml of PBS (4° C.), and the bound radioactivity is determined by scintillation measurement. All the assays are carried out in triplicate. The dissociation constant $K_i$ of the test substance is determined from the IC$_{50}$ of the compounds (concentration of the test substance at which 50% of the ligand bound to the receptor is displaced), the dissociation constant $K_D$ and the concentration L of [$^3$H]-methyllycaconitine using the equation $K_i$=IC$_{50}$/(1+L/K$_D$).

In place of [$^3$H]-methyllycaconitine it is also possible to employ other α7 nAChR-selective radioligands such as, for example, [$^{125}$I]-α-bungarotoxin or nonselective nAChR radioligands together with inhibitors of other nAChRs.

Representative in vitro data for the effect of the compounds of the invention are shown in Table A:

TABLE A

| Example No. | $K_i$ [nM] |
| --- | --- |
| 9 | 519 |
| 14 | 20 |
| 15 | 39 |
| 20 | 10 |
| 21 | 98 |
| 22 | 58 |
| 23 | 39 |
| 24 | 230 |
| 26 | 310 |
| 31 | 420 |

The suitability of the compounds of the invention for the treatment of cognitive impairments can be shown in the following animal models:

2. Object Recognition Test

The object recognition test is a memory test. It measures the ability of rats (and mice) to distinguish between familiar and unfamiliar objects.

The test is carried out as described by Blokland et al., NeuroReport 1998, 9, 4205–4208; A. Ennaceur, J. Delacour, Behav. Brain Res. 1988, 31, 47–59; A. Ennaceur, K. Meliani, Psychopharmacology 1992, 109, 321–330; and Prickaerts et al., Eur. J. Pharmacol. 1997, 337, 125–136.

In a first run, a rat is confronted in an otherwise empty observation arena of relatively large size by two identical objects. The rat will investigate, i.e. sniff round and touch, both objects extensively. In a second run, after an interval of 24 hours, the rat is put in the observation arena again. One of the familiar objects has now been replaced by a new, unfamiliar object. If a rat recognizes the familiar object, it will concentrate on investigating the unfamiliar object. However, after 24 hours, a rat has normally forgotten which object it investigated in the first run, and it will therefore inspect both objects to the same extent. Administration of a substance with a learning- and memory-improving effect may lead to a rat recognizing the object seen in the first run 24 hours previously as familiar. It will investigate the new, unfamiliar object in more detail than the familiar one. This memory ability is expressed in a discrimination index. A discrimination index of zero means that the rat investigates both objects, the old and the new, for equal times; that is to say it has not recognized the old object and reacts to both objects as if they were unfamiliar and new. A discrimination index greater than zero means that the rat inspects the new object longer than the old one; that is to say the rat has recognized the old object.

3. Social Recognition Test:

The social recognition test is a test to examine the learning- or memory-improving effect of test substances.

Adult rats housed in groups are placed singly in test cages 30 minutes before the start of the test. Four minutes before the start of the test, the test animal is put in an observation box. After this adaptation time, a juvenile animal is put in with the test animal and the total time for which the adult animal investigates the juvenile animal is measured for 2 minutes (trial 1). All behaviors clearly directed at the young animal are measured, i.e. anogenital inspection, pursuit and grooming, during which the old animal is no further than 1 cm from the young animal. The juvenile animal is then taken out, and the adult is left in its test cage (for 24-hour retention, the animal is returned to its home cage). The test animal is treated with substance before or after the first test. Depending on the timing of the treatment, the learning or the storage of the information about the young animal can be influenced by the substance. After a fixed period (retention), the test is repeated (trial 2). A larger difference between the investigation times measured in trials 1 and 2 means that the adult animal has remembered the young animal better.

The compounds of the invention of the general formula (I) are suitable for use as medicaments for humans and animals.

The present invention also includes pharmaceutical preparations which, besides inert, nontoxic, pharmaceutically suitable excipients and carriers, contain one or more compounds of the general formula (I), or which consist of one or more compounds of the formula (I), and processes for producing these preparations.

The compounds of the formula (I) are to be present in these preparations in a concentration of from 0.1 to 99.5% by weight, preferably from 0.5 to 95% by weight, of the complete mixture.

Besides the compounds of the formula (I), the pharmaceutical preparations may also contain other active pharmaceutical ingredients.

The abovementioned pharmaceutical preparations can be produced by known methods in a conventional way, for example using the excipient(s) or carrier(s).

The novel active ingredients can be converted in a known manner into conventional formulations such as tablets, coated tablets, pills, granules, aerosols, syrups, emulsions, suspensions and solutions, using inert, nontoxic, pharmaceutically suitable carriers or solvents. In these cases, the therapeutically active compound should in each case be present in a concentration of about 0.5 to 90% by weight of the complete mixture, i.e. in amounts which are sufficient to reach the stated dose range.

The formulations are produced for example by extending the active ingredients with solvents and/or carriers, where appropriate with use of emulsifiers and/or dispersants, it being possible for example when water is used as diluent where appropriate to use organic solvents as auxiliary solvents.

Administration can take place in a conventional way, preferably orally, transdermally or parenterally, especially perlingually or intravenously. However, it can also take place by inhalation through the mouth or nose, for example with the aid of a spray, or topically via the skin.

It has generally proved advantageous to administer amounts of about 0.001 to 10 mg/kg, on oral administration preferably about 0.005 to 3 mg/kg, of body weight to achieve effective results.

It may, nevertheless, be necessary where appropriate to deviate from the stated amounts, in particular as a function of the body weight or of the mode of administration, of the individual behavior towards the medicament, the nature of its formulation and the time or interval over which administration takes place. Thus, it may be sufficient in some cases to make do with less than the aforementioned minimum amount, whereas in other cases the stated upper limit must be exceeded. Where larger amounts are administered, it may be advisable to divide these into a plurality of single doses over the day.

Abbreviations:
DCI direct chemical ionization (in MS)
DMF N,N-dimethylformamide
DMSO dimethyl sulfoxide
EDC N'-(3-dimethylaminopropyl)-N-ethylcarbodiimide×HCl eq. equivalent(s)
ESI electrospray ionization (in MS)
HPLC high pressure, high performance liquid chromatography
LC-MS coupled liquid chromatography/mass spectroscopy
MS mass spectroscopy
NMR nuclear magnetic resonance spectroscopy
PdCl$_2$(dppf) 1,1'-bis(diphenylphosphino)ferrocenepalladium(II) chloride
RT room temperature
R$_t$ retention time (in HPLC)
THF tetrahydrofuran

| LC-MS method A: | |
|---|---|
| MS instrument type: | Micromass Quattro LCZ |
| | Ionization: ESI positive |
| HPLC instrument type: | HP 1100 |
| | UV detector DAD: 208–400 nm |
| | Oven temp.: 40° C. |
| Column: | Symmetry C 18 |
| | 50 mm × 2.1 mm; 3.5 µm |
| Gradient: | Time Flow rate |
| | (min) A: % B: % (ml/min) |
| | 0.00 10.0 90.0 0.50 |
| | 4.00 90.0 10.0 0.50 |
| | 6.00 90.0 10.0 0.50 |
| | 6.10 10.0 90.0 1.00 |
| | 7.50 10.0 90.0 0.50 |
| Eluent A: | Acetonitrile + 0.1% formic acid |
| Eluent B: | Water + 0.1% formic acid |

| LC-MS method B: | |
|---|---|
| MS instrument type: | Micromass Platform LCZ |
| | Ionization: ESI positive |
| HPLC instrument type: | HP 1100 |
| | UV detector DAD: 208–400 nm |
| | Oven temp.: 40° C. |
| Column: | Symmetry C 18 |
| | 50 mm × 2.1 mm; 3.5 µm |
| Gradient: | Time Flow rate |
| | (min) A: % B: % (ml/min) |
| | 0.00 10.0 90.0 0.50 |
| | 4.00 90.0 10.0 0.50 |
| | 6.00 90.0 10.0 0.50 |
| | 6.10 10.0 90.0 1.00 |
| | 7.50 10.0 90.0 0.50 |
| Eluent A: | Acetonitrile + 0.1% formic acid |
| Eluent B: | Water + 0.1% formic acid |

LC-MS Method C:
Instrument: Waters Alliance 2790 LC; column: Symmetry C18, 50 mm×2.1 mm, 3.5 µm; eluent A: water+0.1% formic acid, eluent B: acetonitrile+0.1% formic acid; gradient: 0.0 min 5% B→5.0 min 10% B→6.0 min 10% B; temperature: 50° C.; flow rate: 1.0 ml/min; UV detection: 210 nm.

LC-MS Method D:
Instrument: Micromass Platform LCZ with HPLC Agilent series 1100; column: Grom-SIL120 ODS-4 HE, 50 mm×2.0 mm, 3 µm; eluent A: 1 l of water+1 ml of 50% formic acid; eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208–400 mm.

HPLC Method E:
Instrument: HP 1100 with DAD detection; column: Kromasil RP-18, 60 mm×2 mm, 3.5 µm; eluent A: 5 ml of HClO$_4$/l of water, eluent B: acetonitrile; gradient: 0 min 2% B→0.5 min 2% B→4.5 min 90% B→6.5 min 90% B; flow rate: 0.75 m/min; temperature: 30° C.; UV detection: 210 nm.

LC-MS Method F:
MS instrument: Micromass TOF (LCT); HPLC instrument: 2-column switching, Waters 2690; column: YMC-ODS-AQ, 50 mm×4.6 mm, 3.0 µm; eluent A: water+0.1% formic acid, eluent B: acetonitrile+0.1% formic acid; gradient: 0.0 min 100% A→0.2 min 95% A→1.8 min 25% A→1.9 min 10% A→3.2 min 10% A; flow rate: 3.0 ml/min; oven: 40° C.; UV detection: 210 nm.

Starting Compounds:

EXAMPLE 1A

3-Quinuclidinecarbonyl Chloride Hydrochloride

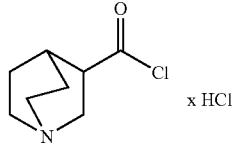

500 mg (2.61 mmol) of 3-quinuclidinecarboxylic acid hydrochloride (Orlek et al., *J. Med. Chem.* 1991, 34, 2726) are boiled together with 1.9 ml (26.09 mmol) of thionyl choride under reflux for 2 h. The reaction mixture is freed of thionyl chloride under reduced pressure. 20 ml portions of toluene are twice added and evaporated to dryness. The product obtained in this way is reacted further without further purification.

EXAMPLE 2A

Quinuclidin-3-one

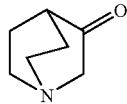

100 g (0.62 mol) of quinuclidin-3-one hydrochloride are suspended in 2 l of methanol. At 0° C., a solution of 33.4 g (0.62 mol) of sodium methoxide in 250 ml of methanol is slowly added dropwise. The mixture is stirred at room temperature for 16 h. The resulting precipitate is filtered off with suction, and the filtrate is concentrated in vacuo. The residue is partitioned between chloroform and water and extracted with chloroform. The combined organic phases are dried over sodium sulfate and concentrated in vacuo. 58.8 g (75.9% of theory) of the title compound are obtained.

MS (DCI): m/z=126 (M+H)$^+$, 143 (M+NH$_4$)$^+$ $^1$H-NMR (300 MHz, CDCl$_3$): δ=3.30 (m, 2H), 3.19–2.86 (m, 4H), 2.46 (m, 1H), 1.99 (m, 4H).

EXAMPLE 3A

Methyl(2Z)-1-azabicyclo[2.2.2]oct-3-ylideneethanoate Hydrochloride

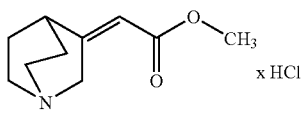

25.3 g (0.63 mol) of sodium hydride (as 60% suspension in mineral oil) are suspended in 480 ml of dimethylformamide. Dropwise addition of a solution of 104.8 g (0.58 mol) of trimethyl phosphonoacetate in 480 ml of dimethylformamide is followed by stirring at room temperature until evolution of hydrogen ceases. A solution of 36 g (0.29 mol) of quinuclidin-3-one in 480 ml of dimethylformamide is added dropwise over a period of 40 minutes and then stirred at room temperature for 16 h. The reaction mixture is concentrated in vacuo, and the residue is partitioned between water and ethyl acetate and extracted with ethyl acetate. The combined organic phases are dried over sodium sulfate and concentrated in vacuo. The residue is purified by column chromatography on silica gel (mobile phase: dichloromethane/methanol/ammonia 95:5:0.5). The material which has been concentrated anew is dissolved in a little dichloromethane, and ethereal HCl is added. The resulting precipitate is filtered off with suction and washed with diethyl ether. Drying at 35° C. results in 19.53 g (31.2% of theory) of the title compound in the form of white crystals.

HPLC (Kromasil RP-18, 60×2.1 mm; eluent A: $H_2O$+5 ml $HClO_4$/l, eluent B: acetonitrile; gradient: 0–4.5 min 98% A→90% B, 4.5–6.5 min 90% B; flow rate: 0.75 ml/min; temp.: 30° C.; UV detection at 210 nm): $R_t$=2.40 min.

MS (DCI): m/z=182 $(M+H)^+$, 199 $(M+NH_4)^+$, 363 $(2M+H)^+$ $^1$H-NMR (500 MHz, DMSO-$d_6$): δ=11.56 (broad s, 1H), 5.97 (m, 1H), 4.32 (m, 2H), 3.66 (s, 3H), 3.27 (m, 4H), 2.84 (m, 1H), 2.13–1.92 (m, 2H), 1.91–1.69 (m, 2H); $^{13}$C-NMR (125 MHz, DMSO-$d_6$): δ=165.72, 155.95, 113.08, 53.55, 51.28, 45.29, 30.14, 22.41.

EXAMPLE 4A

1-Azabicyclo[2.2.2]oct-3-ylacetic acid hydrochloride

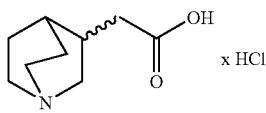

13.5 g (62 mmol) of methyl(2Z)-1-azabicyclo[2.2.2]oct-3-ylidene ethanoate are dissolved in 200 ml of methanol and, under argon, 1 g of palladium on activated carbon (10%) is added. The reaction mixture is stirred under a hydrogen atmosphere (atmospheric pressure) at room temperature for 16 h. It is filtered through kieselguhr and washed with methanol. The filtrate is mixed with 50 ml of 1N hydrochloric acid, concentrated in vacuo and dried under high vacuum. The residue is heated in 100 ml of 32% strength hydrochloric acid to reflux for 5 h. The mixture is concentrated in vacuo, codistilled with toluene twice and dried under high vacuum. 11.8 g of the product are obtained in a purity of 89% (77% of theory).

HPLC (Kromasil RP-18, 60×2.1 mm; eluent A: $H_2O$+5 ml $HClO_4$/l, eluent B: acetonitrile; gradient: 0–4.5 min 98% A→90% B, 4.5–6.5 min 90% B; flow rate: 0.75 ml/min; temp.: 30° C.; UV detection at 210 nm): $R_t$=0.80 min.

MS (DCI): m/z=170 $(M+H)^+$, 339 $(2M+H)^+$ $^1$H-NMR (200 MHz, DMSO-$d_6$): δ=12.32 (broad s, 1H), 10.61 (broad s, 1H), 3.38 (m, 1H), 3.14 (m, 4H), 2.76 (dd, 1H), 2.67–2.22 (m, 4H), 2.01–1.55 (m, 4H).

EXAMPLE 5A

N-(4-Bromophenyl)-1-azabicyclo[2.2.2]octane-3-carboxamide hydrochloride

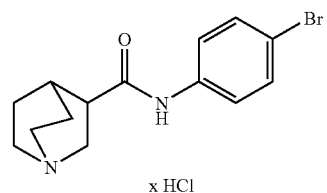

1.00 g (4.76 mmol) of 3-quinuclidinecarbonyl chloride hydrochloride is added at 0° C. to a solution of 900 mg (5.24 mmol) of 4-bromoaniline and 1.85 g (14.28 mmol) of N,N-diisopropylethylamine in about 10 ml of dry DMF. The mixture is stirred at room temperature overnight. Purification by preparative HPLC is followed by chromatography again on silica gel (mobile phase: dichloromethane/methanol/triethylamine 80:20:2). The product is dissolved in methanol and mixed with 1N HCl in methanol. Finally, the solvent is removed. 0.63 g (31% of theory) of the title compound is obtained. The raw material is employed directly in the next synthesis.

LC-MS (method A): $R_t$=2.33 min; MS (ESIpos): m/z=309 $(M+H)^+$ (free base).

EXAMPLE 6A 2-(1-Azabicyclo[2.2.2]oct-3-yl)-N-(4-bromophenyl)acetamide hydrochloride

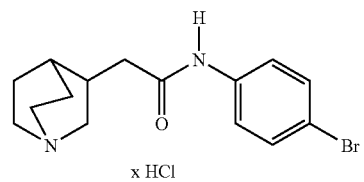

500 mg (2.43 mmol) of 1-azabicyclo[2.2.2]oct-3-ylacetic acid are dissolved in 10 ml of dichloromethane. At 0° C., 1.79 g (9.72 mmol) of pentafluorophenol and 699 mg (3.65 mmol) of N-[3-(dimethylamino)propyl]-N'-ethylcarbodiimide hydrochloride are added. Stirring at room temperature for 14 h is followed by concentration in vacuo, dissolving of the residue in 8 ml of dimethylformamide, addition of 627 mg (3.65 mmol) of p-bromoaniline and stirring further at room temperature for 14 h. 10 ml of 10% strength sodium bicarbonate solution and 10 ml of ethyl acetate are slowly added. The resulting precipitate is filtered off with suction, and the filtrate is extracted three times with ethyl acetate. After drying over sodium sulfate, concentration results in a precipitate, which is filtered off. The solid is suspended in dioxane, mixed with 4M HCl in dioxane and stirred at room temperature for 30 minutes. Renewed filtration of the solid with suction results in 621 mg (71% of theory) of the title compound in the form of white crystals.

HPLC (Kromasil RP-18, 60×2.1 mm; eluent A: $H_2O$+5 ml $HClO_4$/l, eluent B: acetonitrile; gradient=0–4.5 min 98% A→90% B, 4.5–6.5 min 90% B; flow rate: 0.75 ml/min; temp.: 30° C.; UV detection at 210 nm): $R_t$=3.80 min.

MS (ESIpos): m/z=323 (M+H)$^+$ (free base) $^1$H-NMR (200 MHz, DMSO-$d_6$): δ=10.33 (s, 1H), 9.78 (broad s, 1H), 7.63–7.54 (m, 2H), 7.52–7.44 (m, 2H), 3.53–3.05 (m), 2.90 (dd, 1H), 2.71–2.35 (m), 2.00–1.60 (m, 5H).

EXAMPLE 7A 2-(1-Azabicyclo[2.2.2]oct-3-yl)-N-(3-bromophenyl) acetamide Hydrochloride

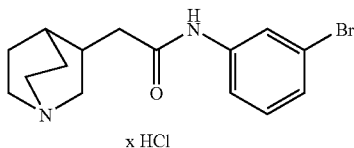

500 mg (2.34 mmol) of 1-azabicyclo[2.2.2]oct-3-ylacetic acid hydrochloride are suspended in 10 ml of dichloromethane and cooled to 0° C. 1.79 g (9.72 mmol) of pentafluorophenol and 699.0 mg (3.65 mmol) of EDC are added, and the mixture is stirred at room temperature overnight. The residue after concentration in vacuo is mixed with 8 ml of DMF and 627.3 mg (3.56 mmol) of 3-bromoaniline and left to stir at room temperature for a further night. The reaction mixture is stirred with 10 ml of 10% strength aqueous sodium bicarbonate solution and 10 ml of ethyl acetate. After the resulting precipitate has been filtered off with suction and washed with ethyl acetate, the two-phase filtrate is separated and the aqueous phase is extracted three times with ethyl acetate. The combined organic phases are dried over sodium sulfate and concentrated. The crude mixture is purified by preparative HPLC. The product fractions are concentrated, taken up in a 5:1 mixture of methanol and 1M hydrochloric acid and again concentrated. Drying under high vacuum results in 600 mg (57.3% of theory) of the title compound, which is employed without further purification in the following stages.

HPLC (method E): $R_t$=3.8 min. LC-MS (method C): m/z=351 (M+H)$^+$ (free base), $R_t$=1.4 min.

EXAMPLE 8A rac-1-Azabicyclo[2.2.2]octane-3-carbonitrile

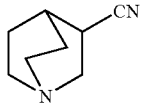

20.4 g (163 mmol) of quinuclidin-3-one and 41.37 g (211.87 mmol) of (4-toluenesulfonyl)methyl isocyanide are introduced into 435 ml of 1,2-dimethoxyethane and 16 ml of dry ethanol while cooling in ice. 45.72 g (407.45 mmol) of potassium tert-butoxide are slowly added in such a way that the temperature does not rise above 10° C. The mixture is then heated at 40° C. for 2.5 h. The solid resulting at RT is filtered off. The filtrate is concentrated and chromatographed on neutral alumina (mobile phase: initially dichloromethane, then ethyl acetate→ethyl acetate/methanol 50:1). 22.9 g (103% of theory) of the product are obtained in slightly impure form.

EXAMPLE 9A

S-1-Azabicyclo[2.2.2]octane-3-carbonitrile

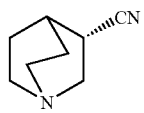

The racemate from Example 8A is separated into the enantiomers by HPLC on a chiral phase [column: Daicel Chiralpak AD 250 mm×20 mm; eluent: 5% water, 87% acetonitrile, 8% acetonitrile with 2% diethylamine; flow rate: 10 ml/min; volume injected: 0.3 ml; UV detection: 220 nm]. 8.3 g (83% of theory) of the title compound are obtained from 20 g of racemic 1-azabicyclo[2.2.2]octane-3-carbonitrile.

HPLC (column: Chiralpak AD 250 mm×4.6 mm, 10 μm; eluent: 5% water, 95% acetonitrile with 2% diethylamine; temperature: 30° C.; flow rate: 1.0 ml/min): $R_t$=5.24 min.

EXAMPLE 10A

R-1-Azabicyclo[2.2.2]octane-3-carbonitrile

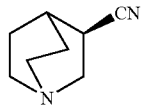

8.7 g (87% of theory) of the title compound are obtained from 20 g of racemic 1-azabicyclo[2.2.2]octane-3-carbonitrile by the process described in Example 9A. HPLC (column: Chiralpak AD 250 mm×4.6 mm, 10 μm; eluent: 5% water, 95% acetonitrile with 2% diethylamine; temperature: 30° C.; flow rate: 1.0 ml/min): $R_t$=6.19 min.

EXAMPLE 11A

S-1-Azabicyclo[2.2.2]octane-3-carboxylic acid

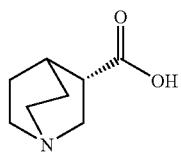

7.60 g (55.80 mmol) of (S)-1-azabicyclo[2.2.2]octane-3-carbonitrile are heated together with 80 ml of concentrated hydrochloric acid under reflux for 4 h. The solvent is removed under reduced pressure and the remaining residual water is removed by distillation with toluene several times. 12.7 g of crude product, which still contains inorganic salts, are obtained and are reacted further without further purification.

EXAMPLE 12A

R-1-Azabicyclo[2.2.2]octane-3-carboxylic acid

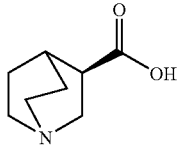

7.50 g (55.07 mmol) of (R)-1-azabicyclo[2.2.2]octane-3-carbonitrile are heated together with 78 ml of concentrated hydrochloric acid under reflux for 4 h. The solvent is removed under reduced pressure and the remaining residual water is removed by distillation with toluene several times. 12.9 g of crude product, which still contains inorganic salts, are obtained and are reacted further without further purification.

EXAMPLE 13A (3S)-N-(4-Bromophenyl)-1-azabicyclo[2.2.2]octane-3-carboxamide

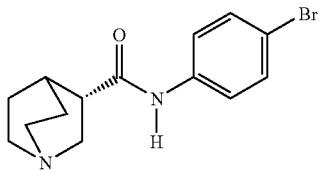

6.6 g (about 34.4 mmol) of (S)-1-azabicyclo[2.2.2]octane-3-carboxylic acid are heated together with 106 ml of thionyl chloride under reflux for 1 h. The excess thionyl chloride is removed under reduced pressure, and residues are removed by azeotropic distillation together with toluene. The crude acid chloride obtained in this way is stirred together with 5.73 g (33.32 mmol) of 4-bromoaniline and 23.21 ml (133.27 mmol) of N,N-diisopropylethylamine in 30 ml of DMF at RT for 72 h. The solvent is removed under reduced pressure. The crude product is purified by chromatography on silica gel 60 (mobile phase: dichloromethane→dichloromethane/methanol/triethylamine 70:30:2). The solvent is removed under reduced pressure. Finally, the last residues of solvent are removed under high vacuum. 2.9 g (28% of theory) of the title compound are isolated in a purity of 76%.

HPLC (method E): $R_t$=3.84 min.

EXAMPLE 14A (3R)-N-(4-Bromophenyl)-1-azabicyclo[2.2.2]octane-3-carboxamide

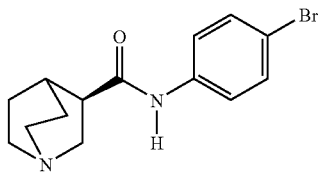

9.17 g (about 47.8 mmol) of (R)-1-azabicyclo[2.2.2]octane-3-carboxylic acid are heated together with 160 ml of thionyl chloride under reflux for 1 h. The excess thionyl chloride is removed under reduced pressure, and residues are removed by azeotropic distillation together with toluene. The crude acid chloride obtained in this way is stirred together with 8.19 g (47.60 mmol) of 4-bromoaniline and 24.6 ml (190.4 mmol) of N,N-diisopropylethylamine in 59 ml of DMF at RT for 72 h. The solvent is removed under reduced pressure. The crude product is purified by chromatography on silica gel 60 (mobile phase: dichloromethane→dichloromethane/methanol/triethylamine 70:30:2). The solvent is removed under reduced pressure. Finally, the last residues of solvent are removed under high vacuum. 5.5 g (37% of theory) of the title compound are obtained. The absolute configuration was assigned by crystal structure analysis of single crystals.

$^1$H-NMR (200 MHz, DMSO-$d_6$): δ=10.06 (s, 1H), 7.70–7.40 (m, 4H), 3.30–3.10 (m, 1H), 2.94–2.45 (m, 6H), 2.15–2.04 (m, 1H), 1.73–1.45 (m, 3H), 1.45–1.15 (m, 1H). HPLC (method E): $R_t$=3.84 min. MS(ESIpos): m/z=309 (M+H)$^+$.

Exemplary Embodiments:

General Method for Synthesizing Exemplary Embodiments 1–4

1.0 eq. of Example 5A, 1.2 eq. of the appropriate boronic acid, 0.1 eq. of 1,1'-bis(diphenylphosphino)ferrocenepalladium(II) chloride and 2.2 eq. of cesium carbonate are heated in 1,2-dimethoxyethane at 90° C. for 60 h. Purification takes place by preparative HPLC chromatography. The purified product is dissolved in methanol and mixed with an excess of 1N HCl in methanol. The solvent is removed in vacuo, and the hydrochloride is dried under high vacuum.

General Method for Synthesizing Exemplary Embodiments 5 and 6

1.0 eq. of Example 6A, 1.0 eq. of the appropriate boronic acid, 0.05 eq. of 1,1'-bis(diphenylphosphino)ferrocenepalladium(II) chloride and 3.0 eq. of 2M sodium carbonate solution are heated in dimethylformamide at 80° C. for 14 h. Filtration through kieselguhr is followed by purification of the products by preparative HPLC chromatography. The purified product is dissolved in methanol and mixed with 4M HCl in dioxane. The solvent is removed in vacuo, and the hydrochloride is dried under high vacuum.

EXAMPLE 1

N-[4-(2-Thienyl)phenyl]-1-azabicyclo[2.2.2]octane-3-carboxamide hydrochloride

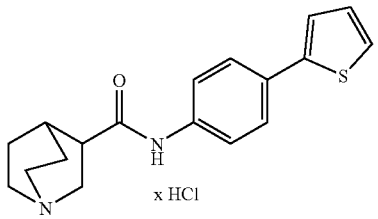

90 mg (0.26 mmol) of N-(4-bromophenyl)-1-azabicyclo[2.2.2]octane-3-carboxamide hydrochloride, 40 mg (0.31 mmol) of 2-thopheneboronic acid, 190 mg (0.57 mmol) of cesium carbonate and 20 mg (0.03 mmol) of bis(diphenylphosphino)ferrocenepalladium(II) chloride are reacted in 1 ml of 1,2-dimethoxyethane by the general method. 14.1 mg (15% of theory) of the title compound are obtained.

LC-MS (method A): $R_t$=2.80 min., MS (ESIpos): m/z=313 (M+H)$^+$ (free base).

EXAMPLE 2

N-[4'-(Hydroxymethyl)-1,1'-biphenyl-4-yl]-1-azabicyclo[2.2.2]octane-3-carboxamide hydrochloride

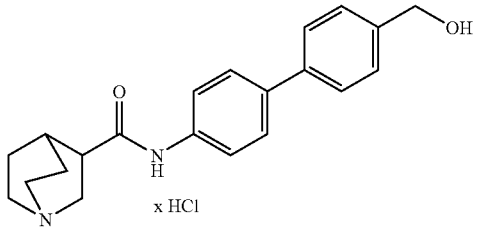

90 mg (0.26 mmol) of N-(4-bromophenyl)-1-azabicyclo[2.2.2]octane-3-carboxamide hydrochloride, 50 mg (0.31 mmol) of 4-(hydroxymethyl)phenylboronic acid, 190 mg (0.57 mmol) of cesium carbonate and 20 mg (0.03 mmol) of bis(diphenylphosphino)ferrocenepalladium(II) chloride are reacted in 1 ml of 1,2-dimethoxyethane by the general method. 5.9 mg (6% of theory) of the title compound are obtained.

LC-MS (method A): $R_t$=2.40 min., MS (ESIpos): m/z=337 (M+H)$^+$ (free base).

EXAMPLE 3

N-(4'-Fluoro-1,1'-biphenyl-4-yl)-1-azabicyclo[2.2.2]octane-3-carboxamide hydrochloride

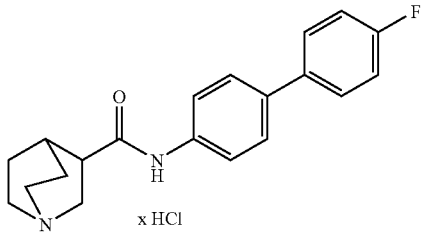

90 mg (0.26 mmol) of N-(4-bromophenyl)-1-azabicyclo[2.2.2]octane-3-carboxamide hydrochloride, 40 mg (0.31 mmol) of 4-fluorophenylboronic acid, 190 mg (0.57 mmol) of cesium carbonate and 20 mg (0.03 mmol) of bis(diphenylphosphino)ferrocenepalladium(II) chloride are reacted in 1 ml of 1,2-dimethoxyethane by the general method. 17.6 mg (19% of theory) of the title compound are obtained.

$^1$H-NMR (200 MHz, DMSO-d$_6$): δ=10.38 (broad s, 1H), 9.83 (broad s, 1H), 7.76–7.57 (m, 6H), 7.33–7.20 (m, 2H), 3.70–3.10 (m, 8H), 2.00–1.65 (m, 4H). LC-MS (method B): $R_t$=2.88 min., MS (ESIpos): m/z=325 (M+H)$^+$ (free base).

EXAMPLE 4

N-(4'-Methylsulfanyl-1,1'-biphenyl-4-yl)-1-azabicyclo[2.2.2]octane-3-carboxamide hydrochloride

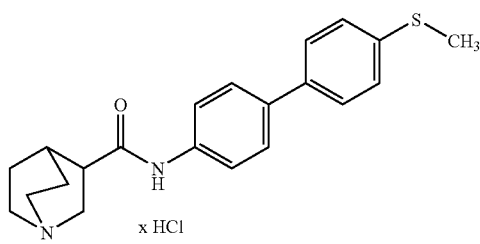

90 mg (0.26 mmol) of N-(4-bromophenyl)-1-azabicyclo[2.2.2]octane-3-carboxamide hydrochloride, 50 mg (0.31 mmol) of 4-(methylsulfanyl)phenylboronic acid, 190 mg (0.57 mmol) of cesium carbonate and 20 mg (0.03 mmol) of bis(diphenylphosphino)ferrocenepalladium(II) chloride are reacted in 1 ml of 1,2-dimethoxyethane by the general method. 21.6 mg (21% of theory) of the title compound are obtained.

LC-MS (method B): $R_t$=3.01 min., MS (ESIpos): m/z=353 (M+H)$^+$ (free base).

EXAMPLE 5

2-(1-Azabicyclo[2.2.2]oct-3-yl)-N-(4'-fluoro-1,1'-biphenyl-4-yl)acetamide hydrochloride

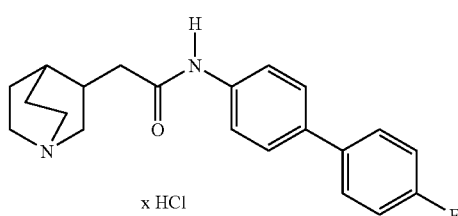

In accordance with the general method, 60 mg (0.17 mmol) of 2-(1-azabicyclo[2.2.2]oct-3-yl)-N-(4-bromophenyl)acetamide hydrochloride, 23.3 mg (0.17 mmol) of 4-fluorophenylboronic acid, 0.17 ml of 2M sodium carbonate solution and 6.1 mg (0.01 mmol) of bis(diphenylphosphino)ferrocenepalladium(II) chloride are reacted in 1 ml of dimethylformamide. 32 mg (51% of theory) of the title compound are obtained.

$^1$H-NMR (200 MHz, DMSO-d$_6$): δ=10.27 (s, 1H), 9.81 (s, 1H), 7.75–7.56 (m, 6H), 7.27 (m, 2H), 3.55–3.30 (m), 3.21 (m, 4H), 2.92 (dd, 1H), 2.76–2.40 (m), 2.05–1.61 (m, 5H). MS (ESIpos): m/z=339 (M+H)$^+$ (free base)

HPLC (Kromasil RP-18, 60×2.1 mm; eluent A: H$_2$O+5 ml HClO$_4$/l, eluent B: acetonitrile; gradient: 0–4.5 min 98% A→90% B, 4.5–6.5 min 90% B; flow rate: 0.75 ml/min; temp.: 30° C.; UV detection at 210 nm): R$_t$=4.20 min.

EXAMPLE 6

2-(1-Azabicyclo[2.2.2]oct-3-yl)-N-(4'-methoxy-1,1'-biphenyl-4-yl)acetamide hydrochloride

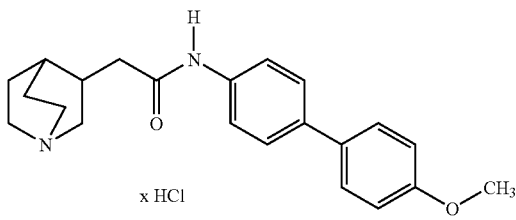

In accordance with the general method, 60 mg. (0.17 mmol) of 2-(1-azabicyclo[2.2.2]oct-3-yl)-N-(4-bromophenyl)acetamide hydrochloride, 25.4 mg (0.17 mmol) of 4-methoxyphenylboronic acid, 0.17 ml of 2M sodium carbonate solution and 6.1 mg (0.01 mmol) of bis(diphenylphosphino)ferrocenepalladium(II) chloride are reacted in 1 ml of dimethylformamide. 34 mg (50% of theory) of the title compound are obtained.

MS (ESIpos): m/z=351 (M+H)$^+$ (free base) HPLC (Kromasil RP-18, 60×2.1 mm; eluent A: H$_2$O+5 ml HClO$_4$/l, eluent B: acetonitrile; gradient: 0–4.5 min 98% A→90% B, 4.5–6.5 min 90% B; flow rate: 0.75 ml/min; temp.: 30° C.; UV detection at 210 nm): R$_t$=4.10 min.

EXAMPLE 7

2-(1-Azabicyclo[2.2.2]oct-3-yl)-N-(4'-fluoro-1,1'-biphenyl-3-yl)acetamide Hydrochloride

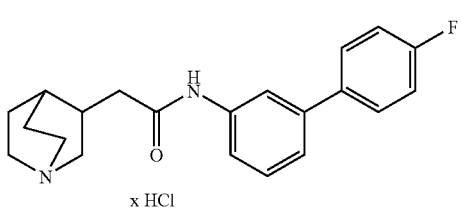

22.1 mg (0.16 mmol) of 4-fluorophenylboronic acid, 0.17 ml (0.34 mmol) of 2M aqueous sodium carbonate solution and 5.8 mg (0.01 mmol) of 1,1'-bis(diphenylphosphino)ferrocenepalladium(II) chloride are added to a solution of 75 mg (0.16 mmol) of 2-(1-azabicyclo[2.2.2]oct-3-yl)-N-(3-bromophenyl)acetamide hydrochloride in 1 ml of DMF. The reaction mixture is stirred at 80° C. overnight. A further 22.1 mg (0.16 mmol) of 4-fluorophenylboronic acid, 23.2 mg (0.03 mmol) of 1,1'-bis(diphenylphosphino)ferrocenepalladium(II) chloride and 0.48 ml (0.48 mmol) of 1M sodium hydroxide solution are added. The mixture is then heated at 80° C. for a further 12 h. After the reaction is complete, the mixture is cooled, filtered through silica gel and then purified by preparative HPLC. The product fractions are concentrated, taken up in methanol, mixed with 4M HCl in dioxane and again concentrated. Drying under high vacuum results in 49.6 mg (83.4% of theory) of the title compound.

HPLC (method E): R$_t$=4.2 min. MS (DCI): m/z=339 (M+H)$^+$ (free base).

EXAMPLE 8

2-(1-Azabicyclo[2.2.2]oct-3-yl)-N-(3'-nitro-1,1'-biphenyl-4-yl)acetamide hydrochloride

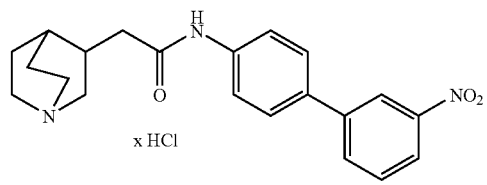

61.3 mg (0.37 mmol) of 3-nitrophenylboronic acid, 0.5 ml (1.0 mmol) of 2M aqueous sodium carbonate solution and 12.2 mg (0.02 mmol) of 1,1'-bis(diphenylphosphino)ferrocenepalladium(II) chloride are added to a solution of 120 mg (0.33 mmol) of 2-(1-azabicyclo[2.2.2]oct-3-yl)-N-(4-bromophenyl)acetamide hydrochloride in 2 ml of DMF. The reaction mixture is stirred at 80° C. for 14 h, cooled, filtered through kieselguhr and then purified by preparative HPLC. The product fractions are concentrated, taken up in a 5:1 mixture of methanol and 1M hydrochloric acid and again concentrated. Drying under high vacuum results in 13 mg (9.7% of theory) of the title compound.

HPLC (method E): R$_t$=4.1 min. MS (DCI): m/z=366 (M+H)$^+$ (free base).

EXAMPLE 9

2-(1-Azabicyclo[2.2.2]oct-3-yl)-N-[4'-(hydroxymethyl)-1,1'-biphenyl-3-yl]acetamide Hydrochloride

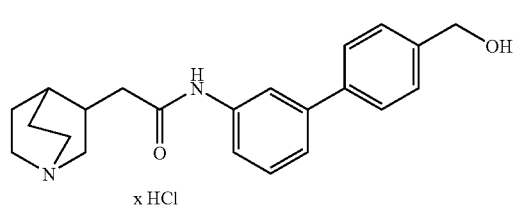

24.0 mg (0.16 mmol) of 4-(hydroxymethyl)phenylboronic acid, 0.17 ml (0.34 mmol) of 2M aqueous sodium carbonate solution and 5.8 mg (0.01 mmol) of 1,1'-bis(diphenylphosphino)ferrocenepalladium(II) chloride are added to a solution of 75 mg (0.16 mmol) of 2-(1-azabicyclo[2.2.2]oct-3-yl)-N-(3-bromophenyl)acetamide hydrochloride in 1 ml of DMF. The reaction mixture is stirred at 80° C. for 14 h. A further 24.0 mg (0.16 mmol) of 4-(hydroxymethyl)phenylboronic acid, 23.2 mg (0.03 mmol) of 1,1'-bis(diphenylphosphino)ferrocenepalladium(II) chloride and 0.48 ml (0.48 mmol) of 1M sodium hydroxide solution are added. The mixture is then heated at 80° C. for a further 12 h. After the reaction is complete, the mixture is cooled, filtered through silica gel and then purified by preparative HPLC. The product fractions are concentrated, taken up in methanol, mixed with 4M HCl in dioxane and again concentrated. Drying under high vacuum results in 25.9 mg (39.8% of theory) of the title compound.

HPLC (method E): $R_t$=3.7 min. MS (DCI): m/z=351 $(M+H)^+$ (free base).

EXAMPLE 10

2-(1-Azabicyclo[2.2.2]oct-3-yl)-N-[4'-(bromomethyl)-1,1'-biphenyl-4-yl]acetamide Hydrochloride

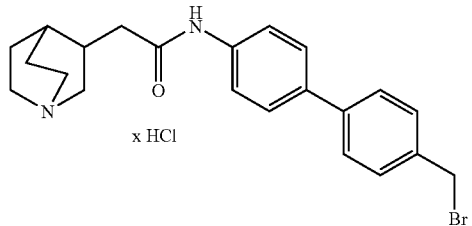

59.7 mg (0.28 mmol) of 4-(brombmethyl)phenylboronic acid, 0.17 ml (0.34 mmol) of 2M aqueous sodium carbonate solution and 10.7 mg (0.01 mmol) of 1,1'-bis(diphenylphosphino)ferrocenepalladium(II) chloride are added to a solution of 100 mg (0.28 mmol) of 2-(1-azabicyclo[2.2.2]oct-3-yl)-N-(4-bromophenyl)acetamide hydrochloride in 1.5 ml of DMF. The reaction mixture is stirred at 80° C. for 14 h, cooled, filtered through silica gel and then purified by preparative HPLC. The product fractions are concentrated, taken up in methanol, mixed with 4M HCl in dioxane and again concentrated. Drying under high vacuum results in 20 mg (16% of theory) of the title compound.

HPLC (method E): $R_t$=4.6 min. MS (ESIpos): m/z=413 $(M+H)^+$ (free base).

EXAMPLE 11

2-(1-Azabicyclo[2.2.2]oct-3-yl)-N-[2'-(hydroxymethyl)-1,1'-biphenyl-3-yl]acetamide Hydrochloride

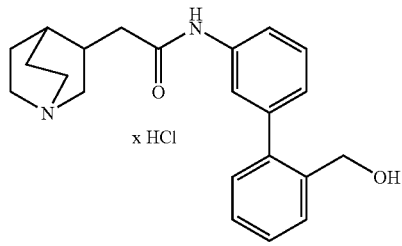

48.1 mg (0.32 mmol) of 2-(hydroxymethyl)phenylboronic acid, 0.95 ml (0.95 mmol) of 1M sodium hydroxide solution and 51.7 mg (0.06 mmol) of 1,1'-bis(diphenylphosphino)ferrocenepalladium(II) chloride are added to a solution of 150 mg (0.32 mmol) of 2-(1-azabicyclo[2.2.2]oct-3-yl)-N-(3-bromophenyl)acetamide hydrochloride in 2 ml of DMF. The reaction mixture is stirred at 80° C. for 18 h. The same amounts of 2-(hydroxymethyl)phenylboronic acid, 1,1'-bis(diphenylphosphino)ferrocenepalladium(II) chloride and sodium hydroxide solution are again added, and the mixture is heated at 80° C. for a further 24 h. The reaction mixture is cooled, filtered through kieselguhr and then purified by preparative HPLC. The product fractions are concentrated, taken up in methanol, mixed with 4M HCl in dioxane and again concentrated. Drying under high vacuum results in 86.5 mg (64.1% of theory) of the title compound.

HPLC (method E): $R_t$=4.3 min. LC-MS (method D): m/z=351 $(M+H)^+$ (free base), $R_t$=2.6 min.

EXAMPLE 12

N-[3'-(Acetylamino)-1,1'-biphenyl-4-yl]-2-(1-azabicyclo[2.2.2]oct-3-yl)acetamide Hydrochloride

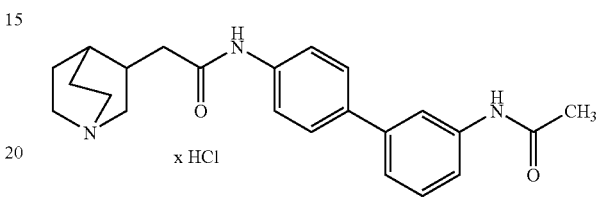

43.8 mg (0.24 mmol) of 3-(acetamido)phenylboronic acid, 0.33 ml (0.66 mmol) of 2M aqueous sodium carbonate solution and 8.1 mg (0.01 mmol) of 1,1'-bis(diphenylphosphino)ferrocenepalladium(II) chloride are added to a solution of 80 mg (0.22 mmol) of 2-(1-azabicyclo[2.2.2]oct-3-yl)-N-(4-bromophenyl)acetamide hydrochloride in 1.5 ml of DMF. The reaction mixture is stirred at 80° C. for 0.14 h, cooled, filtered through kieselguhr and then purified by preparative HPLC. The product fractions are concentrated, taken up in methanol, mixed with 4M HCl in dioxane and again concentrated. Drying under high vacuum results in 23 mg (20% of theory) of the title compound.

HPLC (method E): $R_t$=3.6 min. MS (ESIpos): m/z=378 $(M+H)^+$ (free base).

EXAMPLE 13

(3R)-N-[2'-(Hydroxymethyl)-1,1'-biphenyl-4-yl]-1-azabicyclo[2.2.2]octane-3-carboxamide

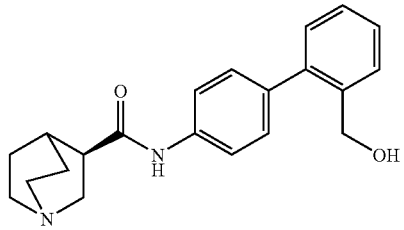

A mixture of 90 mg (0.58 mmol) of 2-(hydroxymethyl)phenylboronic acid, 120 mg (0.39 mmol) of (3R)-N-(4-bromophenyl)-1-azabicyclo[2.2.2]octane-3-carboxamide, 1.16 ml (1.16 mmol) of 1N sodium hydroxide solution, 30 mg (0.04 mmol) of 1,1'-bis(diphenylphosphino)ferrocenepalladium(II) chloride and 1 ml of DMF is heated at 80–85° C. for 42 h. The solvent is removed under reduced pressure. The crude product is purified by chromatography on silica gel 60 (mobile phase: dichloromethane→dichloromethane/methanol/ammonia 80:20:2). 56 mg (39% of theory) of the title compound are obtained.

$^1$H-NMR (400 MHz, DMSO-$d_6$): δ=10.06 (s, 1H), 8.29 (s, 1H), 7.65 (d, 2H), 7.55 (d, 1H), 7.40–7.12 (m, 4H), 4.41 (s,

2H), 3.41–3.22 (m, 1H), 3.03–2.70 (m, 6H), 2.22–2.15 (m, 1H), 1.77–1.58 (m, 3H), 1.52–1.38 (m, 1H). HPLC (method E): $R_t$=3.69 min. LC-MS (method B): $R_t$=2.47 min., MS (ESIpos): m/z=337 (M+H)⁺.

EXAMPLE 14

(3R)-N-[4'-(Hydroxymethyl)-1,1'-biphenyl-4-yl]-1-azabicyclo[2.2.2]octane-3-carboxamide Hydrochloride

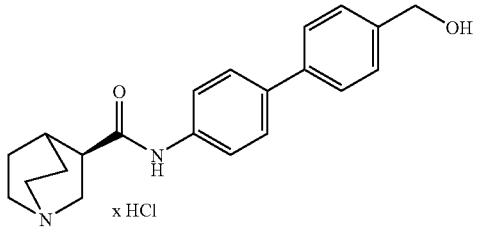

A mixture of 90 mg (0.58 mmol) of 4-(hydroxymethyl)phenylboronic acid, 120 mg (0.39 mmol) of (3R)-N-(4-bromophenyl)-1-azabicyclo[2.2.2]octane-3-carboxamide, 1.16 ml (1.16 mmol) of 1N sodium hydroxide solution, 30 mg (0.04 mmol) of 1,1'-bis(diphenylphosphino)ferrocenepalladium(II) chloride and 1 ml of DMF is heated at 80–85° C. for 42 h. The solvent is removed under reduced pressure. The crude product is purified by chromatography on silica gel 60 (mobile phase: dichloromethane→dichloromethane/methanol/ammonia 80:20:2). This is followed by a final purification by preparative HPLC. The product is dissolved in methanol and mixed with an excess of HCl in diethyl ether. The solvent is stripped off under reduced pressure, and final residues of solvent are removed under high vacuum. 68 mg (47% of theory) of the title compound are obtained.

¹H-NMR (300 MHz, DMSO-$d_6$): δ=10.45 (s, 1H), 10.25 (s, 1H), 7.73–7.52 (m, 6H), 7.40–7.32 (m, 2H), 5.15 (s, 1H), 4.52 (s, 2H), 3.63–3.52 (m, 1H), 3.42–3.00 (m, 7H), 1.98–1.88 (m, 2H), 1.80–1.68 (m, 2H). HPLC (method E): $R_t$=3.54 min. MS (ESIpos): m/z=337 (M+H)⁺.

EXAMPLE 15

(3S)-N-[4'-(Hydroxymethyl)-1,1'-biphenyl-4-yl]-1-azabicyclo[2.2.2]octane-3-carboxamide Hydrochloride

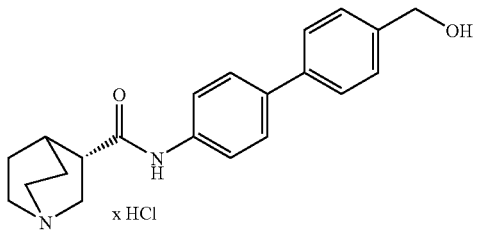

A mixture of 90 mg (0.58 mmol) of 4-(hydroxymethyl)phenylboronic acid, 120 mg (0.39 mmol) of (3S)-N-(4-bromophenyl)-1-azabicyclo[2.2.2]octane-3-carboxamide, 1.16 ml (1.16 mmol) of 1N sodium hydroxide solution, 30 mg (0.04 mmol) of 1,1'-bis(diphenylphosphino)ferrocenepalladium(II) chloride and 1 ml of DMF is heated at 80–85° C. for 42 h. The solvent is removed under reduced pressure. The crude product is purified by chromatography on silica gel 60 (mobile phase: dichloromethane→dichloromethane/methanol/ammonia 80:20:2). This is followed by a final purification by preparative HPLC. The product is dissolved in methanol and mixed with an excess of HCl in diethyl ether. The solvent is stripped off under reduced pressure, and final residues of solvent are removed under high vacuum. 37 mg (26% of theory) of the title compound are obtained.

The analytical data agree with those for the R enantiomer (Example 14).

EXAMPLE 16

(3R)-N-[4'-(4-Morpholinyl)-1,1'-biphenyl-4-yl]-1-azabicyclo[2.2.2]octane-3-carboxamide

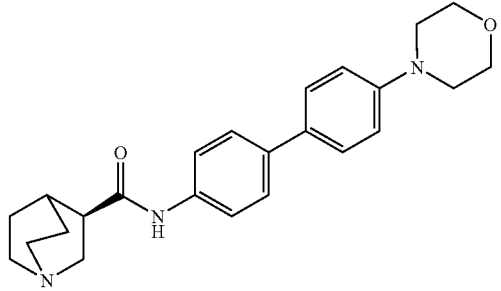

A mixture of 120 mg (0.58 mmol) of 4-morpholinophenylboronic acid, 120 mg (0.39 mmol) of (3R)-N-(4-bromophenyl)-1-azabicyclo[2.2.2]octane-3-carboxamide, 1.16 ml (1.16 mmol) of 1N sodium hydroxide solution, 30 mg (0.04 mmol) of 1,1'-bis(diphenylphosphino)ferrocenepalladium(II) chloride and 1 ml of DMF is heated at 80–85° C. for 40 h. The solvent is removed under reduced pressure. The crude product is purified by chromatography on silica gel 60 (mobile phase: dichloromethane→dichloromethane/methanol/ammonia 80:20:2). The solvent is stripped off under reduced pressure, and final residues of solvent are removed under high vacuum. 100 mg (66% of theory) of the title compound are obtained.

¹H-NMR (400 MHz, DMSO-$d_6$): δ=10.11 (s, 1H), 8.22 (s, 1H), 7.67–7.45 (m, 6H), 6.97 (m, 2H), 3.75 (m, 4H), 3.45–3.37 (m, 1H), 3.15–2.75 (m, 7H), 2.77 (m, 4H), 1.80–1.62 (m, 3H), 1.58–1.48 (m, 1H). HPLC (method E): $R_t$=3.42 min. MS (DCI/NH₃): m/z=392 (M+H)⁺.

EXAMPLE 17

(3R)-N-[4'-(Hydroxymethyl)-3'-(methoxy)-1,1'-biphenyl-4-yl]-1-azabicyclo[2.2.2]-octane-3-carboxamide

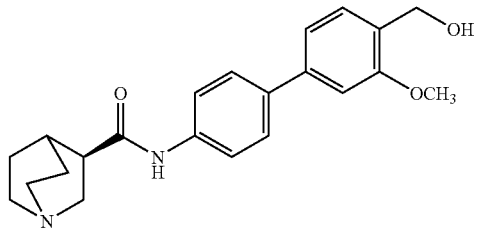

118 mg (0.47) of bis(pinacolato)diboron, 193 mg (1.4 mmol) of dry potassium carbonate, and (4-bromo-2-methoxyphenyl)methanol are dissolved in 1 ml of DMF. Argon is passed through the reaction mixture for 15 minutes, and then 14.2 mg (0.02 mmol) of PdCl$_2$(dppf) are added, and the mixture is heated at 85° C. overnight. Then, 120 mg (0.39 mmol) of (3R)-N-(4-bromophenyl)-1-azabicyclo[2.2.2]octane-3-carboxamide, 1.94 ml of 1N sodium hydroxide solution and a further 14.2 mg (0.02 mmol) of PdCl$_2$(dppf) are added. The mixture is heated at 85° C. overnight. The solvent is removed under reduced pressure. The crude product is purified by chromatography on silica gel 60 (mobile phase: dichloromethane→dichloromethane/methanol/ammonia 60:40:2). The solvent is stripped off under reduced pressure, and final residues of solvent are removed under high vacuum. 5 mg (4% of theory) of the title compound are obtained.

$^1$H-NMR (200 MHz, DMSO-d$_6$): δ=10.38 (s, 1H), 7.80–7.10 (m, 7H), 5.03 (m, 1H), 4.51 (s, 2H), 3.85 (s, 3H), 3.70–2.95 (m, 8H), 2.01–1.63 (m, 4H). HPLC (method E): R$_t$=3.64 min. MS (ESIpos): m/z=367 (M+H)$^+$.

EXAMPLE 18

Methyl 4'-{[(3S)-1-azabicyclo[2.2.2]oct-3-ylcarbonyl]amino}-1,1'-biphenyl-4-carboxylate

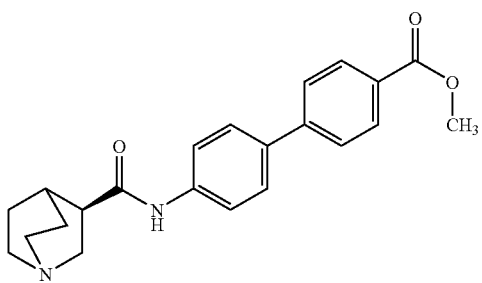

679 mg (3.91 mmol) of (3R)-1-azabicyclo[2.2.2]octane-3-carbonyl chloride, 846 mg (3.73 mmol) methyl 4'-amino-1,1'-biphenyl-4-carboxylate, 963 mg (7.45 mmol) of N,N-diisopropylethylamine and 227 mg (1.86 mmol) of 4-N,N-dimethylaminopyridine are dissolved in 5 ml of THF and stirred at RT overnight and then at 50° C. overnight once again. The reaction mixture is taken up in dichloromethane and water, and the aqueous phase is extracted three times with dichloromethane. The crude product is purified by chromatography on silica gel 60 (mobile phase: dichloromethane/triethylamine 100:1→dichloromethane/methanol/triethylamine 50:50:1). The solvent is removed under reduced pressure. The product is taken up in 1N sodium hydroxide solution and extracted a total of three times with ethyl acetate. The organic phase is dried over magnesium sulfate and freed of solvent under reduced pressure. Finally, the last residues of solvent are removed under high vacuum. 50 mg (4% of theory) of the title compound are obtained.

$^1$H-NMR (300 MHz, DMSO-d$_6$): δ=10.00 (s, 1H), 8.05–7.63 (m, 8H), 3.85 (s, 3H), 3.40–2.65 (m, 8H), 1.70–1.25 (m, 4H). HPLC (method E): R$_t$=4.11 min. MS (ESIpos): m/z=365 (M+H)$^+$.

EXAMPLE 19

4'-{[(3S)-1-Azabicyclo[2.2.2]oct-3-ylcarbonyl]amino}-1,1'-biphenyl-4-carboxylic Acid Hydrochloride

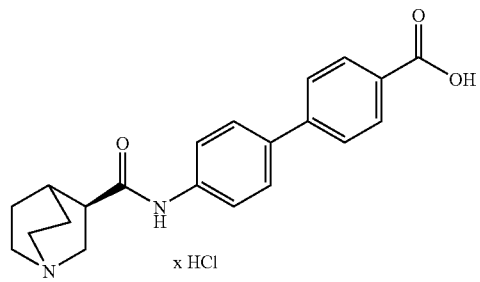

100 mg (0.27 mmol) of methyl 4'-{[(3S)-1-azabicyclo[2.2.2]oct-3-ylcarbonyl]amino}-1,1'-biphenyl-4-carboxylate are suspended in 2 ml of methanol. 200 mg (3.54 mmol) of potassium hydroxide and a few drops of water are added. The mixture is heated under reflux overnight. The solvent is removed under reduced pressure. The residue is mixed with 1N hydrochloric acid, whereupon the product precipitates. It is filtered off and washed with a little water. 60 mg (57% of theory) of the title compound are obtained.

$^1$H-NMR (200 MHz, DMSO-d$_6$): δ=10.50 (s, 1H), 9.95 (s, 1H), 8.05–7.63 (m, 8H), 3.70–3.05 (m, 8H), 2.05–1.65 (m, 4H). HPLC (method E): R$_t$=3.56 min. MS (ESIpos): m/z=351 (M+H)$^+$.

EXAMPLE 20

(3R)-N-[4'-(1-Hydroxy-1-methylethyl)-1,1'-biphenyl-4-yl]-1-azabicyclo[2.2.2]octane-3-carboxamide

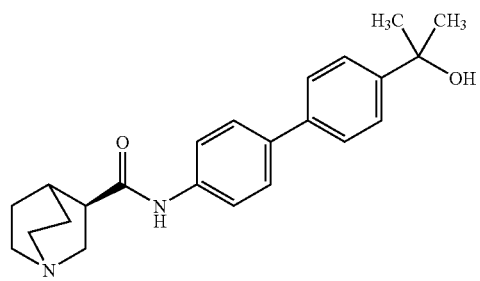

230 mg (0.63 mmol) of methyl 4'-{[(3S)-1-azabicyclo[2.2.2]oct-3-ylcarbonyl]amino}-1,1'-biphenyl-4-carboxylate, suspended in 1 ml of THF, are added to 5.75 ml (8.05 mmol) of methylmagnesium bromide (1.6M solution in 1:1 THF/toluene) at 0° C. under argon. The reaction mixture is stirred at RT overnight. While cooling in ice, 1N sodium hydroxide solution is added, and the mixture is extracted five times with ethyl acetate. The combined organic phases are dried over magnesium sulfate. The crude product is purified on silica gel 60 (mobile phase: dichloromethane/methanol/ammonia 90:10:1→80:20:1). The solvent is removed under reduced pressure. 193 mg (81% of theory) of the title compound are obtained.

HPLC (method E): R$_t$=3.82 min. MS (ESIpos): m/z=365 (M+H)$^+$.

EXAMPLE 21

(3R)-N-[4'-(Aminocarbonyl)-1,1'-biphenyl-4-yl]-1-azabicyclo[2.2.2]octane-3-carboxamide Hydrochloride

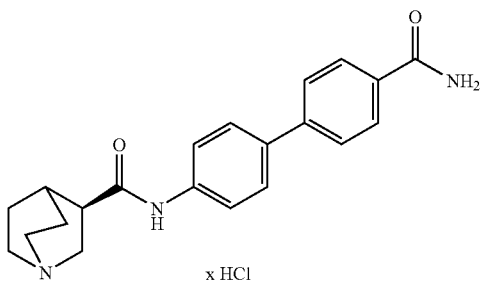

60 mg (0.16 mmol) of 4'-{[(3S)-1-azabicyclo[2.2.2]oct-3-ylcarbonyl]amino}-1,1'-biphenyl-4-carboxylic acid hydrochloride and 2 ml (27.4 mmol) of thionyl chloride are heated under reflux for 3 h. The excess of thionyl chloride is distilled off. The crude acid chloride prepared in this way is introduced into 1 ml of THF and stirred with 3.1 ml (1.55 mmol) of ammonia (0.5M solution in dioxane) at RT for three days. The solvent is removed under reduced pressure, and the crude product is purified by preparative HPLC. 11 mg (18% of theory) of the title compound are obtained.

HPLC (method E): $R_t$=3.30 min. MS (ESIpos): m/z=350 (M+H)$^+$.

EXAMPLE 22

(3R)-N-[4'-(Hydroxymethyl)-3'-fluoro-1,1'-biphenyl-4-yl]-1-azabicyclo[2.2.2]octane-3-carboxamide

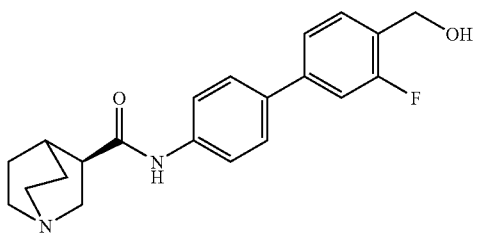

492 mg (1.62) of bis(pinacolato)diboron, 804 mg (5.82 mmol) of dry potassium carbonate, and 398 mg (1.94 mmol) of (4-bromo-2-fluorophenyl)methanol are dissolved in 4.2 ml of DMF. Argon is passed through the reaction mixture for 15 minutes, and then 59 mg (0.08 mmol) of PdCl$_2$(dppf) are added, and the mixture is heated at 85° C. overnight. Then, 500 mg (1.62 mmol) of (3R)-N-(4-bromophenyl)-1-azabicyclo[2.2.2]octane-3-carboxamide, 8.1 ml of 1N sodium hydroxide solution and a further 59 mg (0.02 mmol) of PdCl$_2$(dppf) are added. The mixture is heated at 85° C. overnight. The solvent is removed under reduced pressure. The crude product is purified by preparative HPLC. 21 mg (3% of theory) of the title compound are obtained.

$^1$H-NMR (400 MHz, CD$_3$OD): δ=8.52 (s, 1H), 7.70–7.25 (m, 7H), 4.51 (s, 2H), 3.92–3.75 (m, 1H), 3.50–3.10 (m, 6H), 2.58–2.46 (m, 1H), 2.21–1.94 (m, 3H), 1.93–1.76 (m, 1H). HPLC (method E): $R_t$=3.66 min. MS (ESIpos): m/z=355 (M+H)$^+$.

EXAMPLE 23

(4'-{[(3R)-1-Azabicyclo[2.2.2]oct-3-ylcarbonyl]amino}-1,1'-biphenyl-4-yl)methyl Methylcarbamate

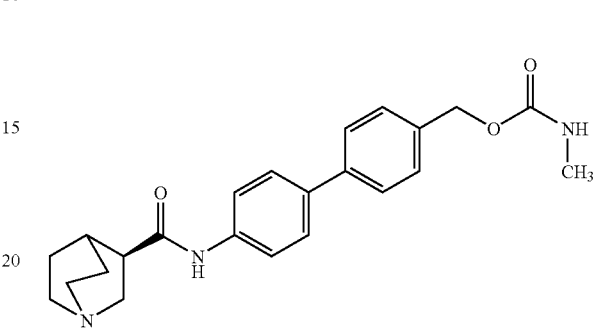

35 mg (0.10 mmol) of (3R)-N-[4'-(hydroxymethyl)-1,1'-biphenyl-4-yl]-1-azabicyclo-[2.2.2]octane-3-carboxamide are dissolved in 1 ml of a 1:1 THF/DMF mixture. 12 mg (0.21 mmol) of methyl isocyanate are added, and the mixture is stirred at 60° C. overnight. The solvent is removed under reduced pressure, and the crude product is purified by preparative HPLC. 20 mg (49% of theory) of the title compound are obtained.

HPLC (method E): $R_t$=3.80 min. MS (ESIpos): m/z=394 (M+H)$^+$.

EXAMPLE 24

(4'-{[(3R)-1-Azabicyclo[2.2.2]oct-3-ylcarbonyl]amino}-1,1'-biphenyl-4-yl)methyl Isopropylcarbamate

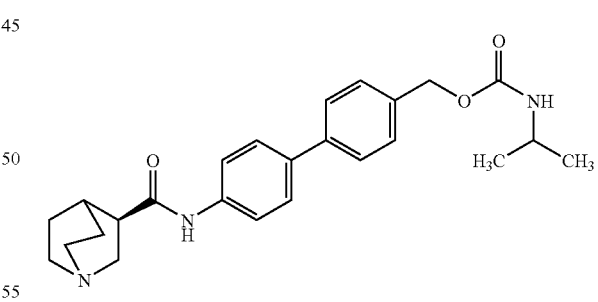

35 mg (0.10 mmol) of (3R)-N-[4'-(hydroxymethyl)-1,1'-biphenyl-4-yl]-1-azabicyclo-[2.2.2]octane-3-carboxamide are dissolved in 1 ml of a 1:1 THF/DMF mixture. 17 mg (0.21 mmol) of isopropyl isocyanate are added, and the mixture is stirred at 60° C. overnight. The solvent is removed under reduced pressure, and the crude product is purified by preparative HPLC. 23 mg (52% of theory) of the title compound are obtained.

HPLC (method E): $R_t$=4.13 min. MS (ESIpos): m/z=422 (M+H)$^+$.

EXAMPLE 25

(4'-{[(3R)-1-Azabicyclo[2.2.2]oct-3-ylcarbonyl]amino}-1,1'-biphenyl-4-yl)methyl Ethylcarbamate

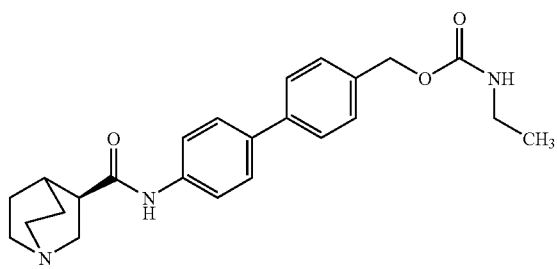

35 mg (0.10 mmol) of (3R)-N-[4'-(hydroxymethyl)-1,1'-biphenyl-4-yl]-1-azabicyclo-[2.2.2]octane-3-carboxamide are dissolved in 1 ml of a 1:1 THF/DMF mixture. 17 mg (0.21 mmol) of ethyl isocyanate are added, and the mixture is stirred at 60° C. overnight. The solvent is removed under reduced pressure, and the crude product is purified by preparative HPLC. 24 mg (55% of theory) of the title compound are obtained.

HPLC (method E): $R_t$=3.97 min. MS (ESIpos): m/z=408 (M+H)$^+$.

General Method for Synthesizing Exemplary Embodiments 26–35

32.3 mg (0.1 mmol) of 2-(1-azabicyclo[2.2.2]oct-3-yl)-N-(4-bromophenyl)acetamide hydrochloride, 0.1 mmol of the appropriate boronic acid, 21.2 mg (0.2 mmol) of sodium carbonate and 3.7 mg (0.01 mmol) of tetrakis(triphenylphosphine)palladium(0) are heated in 0.5 ml of dioxane and 0.1 ml of water at 80° C. overnight. The mixture is diluted with DMSO, filtered and purified by preparative HPLC. The product fractions are mixed with 2N hydrochloric acid and concentrated in vacuo.

| Ex. No. | Structure | LC-MS (method F): [M+H]$^+$ (free base) |
|---|---|---|
| 26 | | 363 |
| 27 | 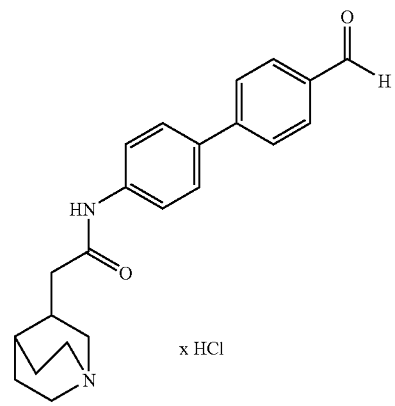 | 349 |
| 28 | 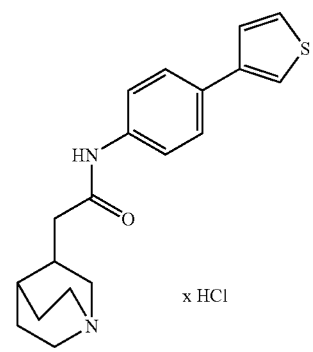 | 327 |
| 29 | 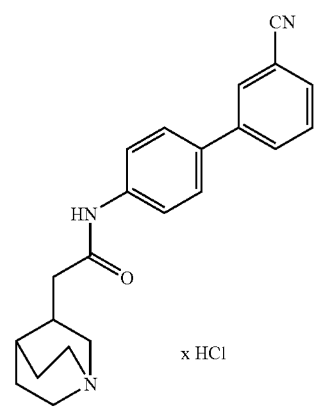 | 346 |
| 30 | 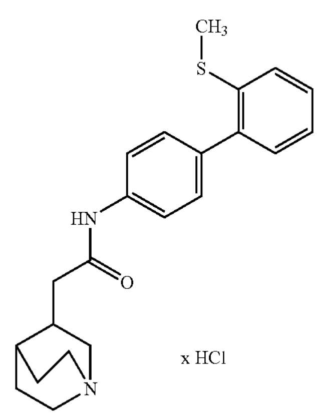 | 367 |

-continued

| Ex. No. | Structure | LC-MS (method F): [M+H]+ (free base) |
|---|---|---|
| 31 | 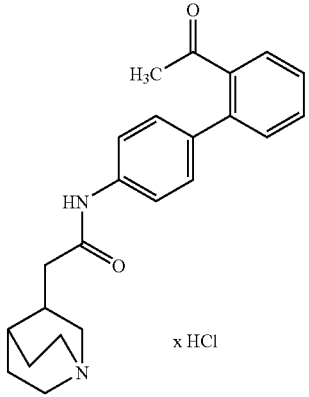 x HCl | 363 |
| 32 | 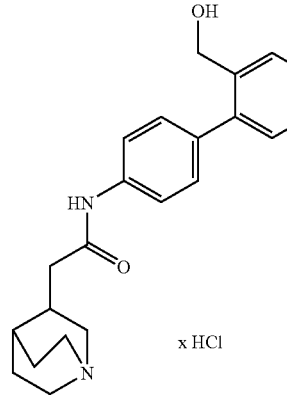 x HCl | 351 |
| 33 | 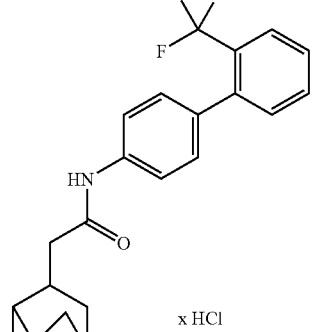 x HCl | 389 |

-continued

| Ex. No. | Structure | LC-MS (method F): [M+H]+ (free base) |
|---|---|---|
| 34 | 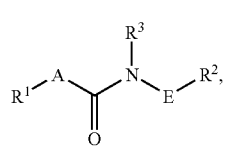 x HCl | 335 |
| 35 |  x HCl | 351 |

The invention claimed is:
1. A compound of the formula (I)

in which
$R^1$ is a 1-azabicyclo[m.n.p]alkyl radical having 7 to 11 ring atoms,
  in which m and n are independently of one another 2 or 3,
  in which p is 1, 2 or 3,
  and where the bicycloalkyl radical is optionally substituted by ($C_1$–$C_6$)-alkyl,
A is a bond, methylene, ethylene or propylene,
E is divalent, 5- to 6-membered heteroaryl or benzenediyl, where heteroaryl and benzenediyl are optionally substituted by radicals selected from the group of halogen, cyano, trifluoromethyl, trifluoromethoxy and ($C_1$–$C_6$)-alkyl,
$R^2$ is 5- to 6-membered heteroaryl or phenyl, where heteroaryl and phenyl are optionally substituted by radicals selected from the group of halogen, 5- to 6-membered heterocyclyl, —CO—$NR^4R^5$, —CO—

OR$^6$, —NR$^7$R$^8$, —NR$^9$—CO—R$^{10}$, —COR$^{13}$, cyano, trifluoromethyl, trifluoromethoxy, nitro, optionally hydroxyl-, amino-, —NH—CO—R$^{11}$—, —O—CO—NHR$^{14}$—, halogen- or cyano-substituted (C$_1$–C$_6$)-alkyl, (C$_1$–C$_6$)-alkoxy and (C$_1$–C$_6$)-alkylthio,
in which R$^4$, R$^5$, R$^6$, R$^7$, R$^8$, R$^9$, R$^{10}$, R$^{11}$, R$^{13}$ and R$^{14}$ are independently of one another hydrogen, (C$_1$–C$_6$)-alkyl, phenyl or benzyl, and
R$^3$ is hydrogen or (C$_1$–C$_6$)-alkyl,
and the salts, solvates and solvates of the salts thereof.

2. A compound as claimed in claim 1, in which
R$^1$ is a 1-azabicyclo[m.n.p]alkyl radical having 7 to 11 ring atoms,
in which m and n are independently of one another 2 or 3,
in which p is 1, 2 or 3,
and where the bicycloalkyl radical is optionally substituted by (C$_1$–C$_6$)-alkyl,
A is a bond, methylene, ethylene or propylene,
E is divalent, 5- to 6-membered heteroaryl or benzenediyl, where heteroaryl and benzenediyl are optionally substituted by radicals selected from the group of halogen, cyano, trifluoromethyl, trifluoromethoxy and (C$_1$–C$_6$)-alkyl,
R$^2$ is 5- to 6-membered heteroaryl or phenyl, where heteroaryl and phenyl are optionally substituted by radicals selected from the group of halogen, formyl, —CO—NR$^4$R$^5$, —CO—OR$^6$, —NR$^7$R$^8$, —NR$^9$—CO—R$^{10}$, cyano, trifluoromethyl, trifluoromethoxy, nitro, optionally hydroxyl-, amino-, —NH—CO—R$^{11}$— or cyano-substituted (C$_1$–C$_6$)-alkyl, (C$_1$–C$_6$)-alkoxy and (C$_1$–C$_6$)-alkylthio,
in which R$^4$, R$^5$, R$^6$, R$^7$, R$^8$, R$^9$, R$^{10}$ and R$^{11}$ are independently of one another hydrogen, (C$_1$–C$_6$)-alkyl, phenyl or benzyl, and
R$^3$ is hydrogen or (C$_1$–C$_6$)-alkyl,
and the salts, solvates and solvates of the salts thereof.

3. A compound as claimed in claim 1, where
R$^1$ is 1-azabicyclo[2.2.2]oct-3-yl,
and A, E, R$^2$ and R$^3$ have the meanings indicated in claim 1.

4. A compound as claimed in claims 1, where
R$^1$ is 1-azabicyclo[2.2.2]oct-3-yl,
A is a bond or methylene,
E is benzenediyl which is optionally substituted by a radical selected from the group of fluorine, chlorine, cyano, methyl and trifluoromethyl,
R$^2$ is thienyl or phenyl, where the rings are optionally substituted by up to 2 radicals selected from the group of halogen, cyano, trifluoromethyl, trifluoromethoxy, nitro, morpholinyl, (C$_1$–C$_4$)-alkyl, (C$_1$–C$_4$)-alkoxy, (C$_1$–C$_4$)-alkylthio, —CO—NR$^4$R$^5$, —CO—OR$^6$, —NR$^9$—CO—R$^{10}$ and —CO—R$^{13}$,
where (C$_1$–C$_4$)-alkyl is optionally substituted by hydroxy, halogen and —O—CO—NHR$^{14}$,
where R$^4$, R$^5$, R$^6$, R$^9$, R$^{10}$, R$^{13}$ and R$^{14}$ are independently of one another hydrogen or (C$_1$–C$_4$)-alkyl, and
R$^3$ is hydrogen,
and the salts, solvates and solvates of the salts thereof.

5. A compound as claimed in claim 1, where
R$^1$ is 1-azabicyclo[2.2.2]oct-3-yl,
A is a bond,
E is benzenediyl which is optionally substituted by 1 to 3 radicals selected from the group of fluorine, chlorine, cyano, methyl and trifluoromethyl, R$^2$ is thienyl or phenyl, where the rings are optionally substituted by 1 to 3 radicals selected from the group of halogen, cyano, trifluoromethyl, trifluoromethoxy, nitro, (C$_1$–C$_4$)-alkyl, hydroxymethyl, and (C$_1$–C$_4$)-alkoxy, and
R$^3$ is hydrogen.

6. A process for preparing compounds as claimed in claims 1 to 5, characterized in that
[A] compounds of the general formula (II)

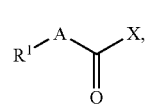

(II)

in which
R$^1$ and A have the meanings indicated in claim 1, and
X is hydroxy or a suitable leaving group,
are reacted with a compound of the general formula (III)

R$^3$—NH-E-R$^2$   (III), in which R$^2$, R$^3$ and E have the meanings indicated in claim 1, or
[B] compounds of the general formula (V)

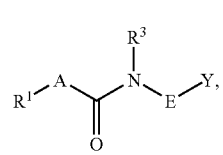

(V)

in which
Y is a suitable leaving group, and
R$^1$, R$^3$, A and E have the meanings indicated in claim 1,
are reacted with compounds of the general formula (VI)

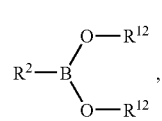

(VI)

in which
R$^2$ has the meanings indicated above, and
R$^{12}$ is hydrogen or methyl, or the two radicals together form a CH$_2$CH$_2$ or C(CH$_3$)$_2$—C(CH$_3$)$_2$ bridge,
in an inert solvent in the presence of a suitable catalyst and in the presence of a base, and the resulting compounds of the formula (I) are where appropriate converted with the appropriate (i) solvents and/or (ii) bases or acids into the solvates, salts and/or solvates of the salts thereof.

7. A medicament comprising at least one of the compounds as claimed in claim 1 in combination with at least one pharmaceutically acceptable, essentially nontoxic carrier or excipient.

8. A method for producing a medicament for improving perception, concentration, learning and/or memory comprising the step of mixing at least one compound as claimed in claim 1 with at least one pharmaceutically acceptable, essentially nontoxic carrier or excipient.

9. A method for the treatment of impairments of perception, concentration, learning and/or memory in humans and animals comprising administering an effective amount of at least one compound as claimed in any of claims 1 to 5.

10. A method for the treatment of impairments of perception, concentration, learning and/or memory comprising administering to a subject an effective amount of the medicament as claimed in claim 7.

11. The process of claim 6, wherein X is a leaving group selected from chlorine and pentafluorophenoxy.

12. The process of claim 6, wherein Y is a leaving group selected from triflate and halogen.

13. The process of claim 12, wherein the halogen is bromine or iodine.

* * * * *